US010821117B2

(12) United States Patent
Voskuhl

(10) Patent No.: US 10,821,117 B2
(45) Date of Patent: *Nov. 3, 2020

(54) ESTROGEN THERAPY FOR BRAIN GRAY MATTER ATROPHY AND ASSOCIATED DISABILITY

(71) Applicant: The Regents of the University of California, Oakland, CA (US)

(72) Inventor: Rhonda R. Voskuhl, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 96 days.

This patent is subject to a terminal disclaimer.

(21) Appl. No.: 15/507,863

(22) PCT Filed: Sep. 1, 2015

(86) PCT No.: PCT/US2015/047906
§ 371 (c)(1),
(2) Date: Mar. 1, 2017

(87) PCT Pub. No.: WO2016/036719
PCT Pub. Date: Mar. 10, 2016

(65) Prior Publication Data
US 2017/0290845 A1    Oct. 12, 2017

Related U.S. Application Data

(60) Provisional application No. 62/044,757, filed on Sep. 2, 2014.

(51) Int. Cl.
*A61K 31/565* (2006.01)
*A61K 31/57* (2006.01)
*A61K 31/566* (2006.01)
*A61K 49/06* (2006.01)

(52) U.S. Cl.
CPC .......... *A61K 31/565* (2013.01); *A61K 31/566* (2013.01); *A61K 31/57* (2013.01); *A61K 49/06* (2013.01)

(58) Field of Classification Search
None
See application file for complete search history.

(56) References Cited

U.S. PATENT DOCUMENTS

| | | | |
|---|---|---|---|
| 3,932,635 A | 1/1976 | Segre | |
| 4,826,831 A | 5/1989 | Plunkett et al. | |
| 5,108,995 A | 4/1992 | Casper | |
| 9,962,395 B2 | 5/2018 | Voskuhl | |
| 10,369,158 B2 | 8/2019 | Voskuhl | |
| 10,406,169 B2 | 9/2019 | Voskuhl | |
| 2005/0113350 A1 | 5/2005 | Duesterberg et al. | |
| 2005/0239758 A1 | 10/2005 | Roby | |
| 2009/0005351 A1 | 1/2009 | Pickar et al. | |
| 2010/0168071 A1 | 7/2010 | Boissonneault | |
| 2010/0203016 A1* | 8/2010 | Voskuhl | A61K 31/56 424/85.6 |
| 2012/0282222 A9* | 11/2012 | Voskuhl | A61K 31/277 424/85.6 |
| 2013/0203722 A1* | 8/2013 | Voskuhl | A61K 31/565 514/182 |
| 2017/0049785 A1 | 2/2017 | Voskuhl | |
| 2017/0290845 A1 | 10/2017 | Voskuhl | |

FOREIGN PATENT DOCUMENTS

| | | |
|---|---|---|
| AU | 2004257772 A1 | 1/2005 |
| WO | WO-01070208 A2 | 9/2001 |
| WO | WO-2002/085364 A1 | 10/2002 |
| WO | WO-2002/085374 | 10/2002 |
| WO | WO-2002/092102 A2 | 11/2002 |
| WO | WO-2002/092102 A3 | 11/2002 |
| WO | WO-2007/038435 A2 | 4/2007 |
| WO | WO-2007/038636 A2 | 4/2007 |
| WO | WO-2008150547 A1 | 12/2008 |
| WO | WO-2010/050916 A1 | 5/2010 |
| WO | WO-2015/168000 A1 | 11/2015 |

OTHER PUBLICATIONS

Bendfeldt et al., Brain Research, 2010; 1325: 174-182 (Year: 2010).*
Zivadinov et al., Multiple Sclerosis 2007; 13: 490-501 (Year: 2007).*
Geurts et al., Lancet Neurol., 2012; 11: 1082-92 (Year: 2012).*
Tolppanen et al., Drugs & Aging, 2018; 35: 985-992 (Year: 2018).*
Ransohoff, Nature Neuroscience, 2012; 15:1074-1077 (Year: 2012).*
Vickers, Drugs Aging, 2002, 19: 487-494 (Year: 2002).*
Lanka and Cudkowicz, Amyotrophic Lateral Sclerosis, 2008; 9:131-140 (Year: 2008).*
The webpage from https://www.mayoclinic.org/diseases-conditions/huntingtons-disease/symptoms-causes/syc-20356117?p=1; 4 pages total; downloaded Oct. 14, 2018 (Year: 2018).*
Gold et al., "Estrogen treatment in multiple sclerosis," J Neurol Sci, 286(1-2):99-103 (2009).
International Search Report of the International Searching Authority, dated Aug. 3, 2015, from related International Application No. PCT/US2015/027756.
International Search Report of the International Searching Authority, dated Aug. 5, 2015, from related International Application No. PCT/US2015/027752.
International Search Report of the International Searching Authority, dated Jan. 10, 2016, from related International Application No. PCT/US2015/047906.
International Search Report of the International Searching Authority, dated Jul. 11, 2016, from related International Application No. PCT/US2016/024754.

(Continued)

*Primary Examiner* — Christina M Borgeest
(74) *Attorney, Agent, or Firm* — Foley Hoag LLP; David P. Halstead; Alexander J. Chatterley

(57) ABSTRACT

Provided are methods for slowing, halting, and reversing gray matter atrophy and progression of disability in certain neurodegenerative diseases, including multiple sclerosis, using estrogen, alone or in combination with another agent.

20 Claims, 9 Drawing Sheets

(56) References Cited

OTHER PUBLICATIONS

International Search Report of the International Searching Authority, dated Feb. 16, 2016, from related International Application No. PCT/US2015/056649.
International Search Report of the International Searching Authority, dated Jul. 21, 2016, from related International Application No. PCT/US2016/024751.
International Search Report of the International Searching Authority, dated Dec. 24, 2015, from related International Application No. PCT/US2015/052805.
Luchetti et al., "Gender Differences in Multiple Sclerosis: Induction of Estrogen Signaling in Male and Progesterone Signaling in Female Lesions," J Neuropathol Exp Neurol, 73(2): 123-135 (2014).
MacKenzie-Graham et al., "Estrogen treatment prevents gray matter atrophy in experimental autoimmune encephalomyelitis," J Neurosci Res, 90(7):1310-23 (2012).
Nicot, "Gender and sex hormones in multiple sclerosis pathology and therapy," Front Biosci (Landmark Ed), 14: 4477-4515 (2009).
Prempro and Premphase drug information, Food and Drug Administration, dated Jun. 5, 2003, Retrieved from the Internet. URL: http://www.fda.gov/ohrms/dockets/ac/03/briefing/3992B1_03_FDA-Prempro-Premphase.pdf.
Sicotte et al., "Treatment of Multiple Sclerosis with the Pregnancy Hormone Estriol," Ann Neurol, 52(4): 421-428 (2002).
Smith et al., "Impact of combined estradiol and norethindrone therapy on visuospatial working memory assessed by functional magnetic resonance imaging," J Clin Endocrinol Metab, 91(11):4476-81 (2006).
Speroff et al., "Postmenopausal hormone therapy," Gynecololgy and Obstetrics, Chapter 110, Mar. 8, 2011. URL: http://www.glowm.com/resources/glowm/cd/pages/v1/v1c110.html.
Alhola et al., "Estrogen+ progestin therapy and cognition: A randomized placebo☐controlled double☐blind study," J Obstet Gynaecol Re, 36(4): 796-802 (2010).
Anderer et al., "Age-related cognitive decline in the menopause: effects of hormone replacement therapy on cognitive event-related potentials," Maturitas, 51(3): 254-269 (2005).
Anderson, "Adding estriol reduces ms relapse rate," Medscape Medical News, pp. 1-4 (2014). [https://www.medscape.com/viewarticle/824364].
Anonymous: "Estriol Treatment in Multiple Sclerosis (MS): Effect on Cognition," ClinicalTrials.gov archive, pp. 1-5 (2013). NCT01466114.
Blasco et al., "Amyotrophic Lateral Sclerosis," Informa Healthcare, 13:585-588 (2012).
Chen et al., "The Treatment Strategies for Neurodegenerative Diseases by Integrative Medicine," Integrative Medicine International, 1:223-225 (2014).
Cubo et al., "Effect of Donepezil on Motor and Cognitive Function in Huntington Disease," Neurology, 67(7):1268-1271 (2006).
Extended European Search Report issued by the European Patent Office in corresponding Application No. 15846358.8, dated Apr. 17, 2018.
Extended European Search Report issued by the European Patent Office in corresponding Application No. EP 15786314.3, dated Dec. 1, 2017.
Extended European Search Report issued by the European Patent Office in corresponding Application No. EP 15786637.7, dated Dec. 1, 2017.
Itoh et al., "Bedside to bench to bedside research: Estrogen receptor beta ligand as a candidate neuroprotective treatment for multiple sclerosis," J Neuroimmunol, 304:63-71 (2017).
Kipp et al., "Multiple sclerosis: neuroprotective alliance of estrogen-progesterone and gender," Front Neuroendocrin, 33(1):1-16 (2012).
Luine, "Estradiol and cognitive function: past, present and future," Horm Behav, 66(4):602-618 (2014).
Rubin, "Parkinson's Disease in Women," American Parkinson Disease Association, https://www.apdaparkinson.org/parkinsons-disease-in-women/ (2015).
Soldan et al., "Immune modulation in multiple sclerosis patients treated with the pregnancy hormone estriol," J Immunol, 171(11):6267-6274 (2003).
Spence et al., "Neuroprotective effects of estrogens and androgens in CNS inflammation and neurodegeneration," Front Neuroendocrinol, 33(1):105-115 (2012).
Voskuhl et al., "Estriol combined with glatiramer acetate for women with relapsing-remitting multiple sclerosis: a randomised, placebo-controlled, phase 2 trial," Lancet Neurol, 15(1):35-46 (2016).
Zhang et al., "Distribution and differences of estrogen receptor beta immunoreactivity in the brain of adult male and female rats," Brain Res, 935(1-2):73-80 (2002).
Aygestin® Label, norethindrone acetate rablets, USP, Rx Only.
Extended European Search Report issued by the European Patent Office in corresponding Application No. PCT/US2016/024754 dated Nov. 21, 2018.
Holtorf et al., "The Bioidentical Hormone Debate: Are Bioidentical Hormones (Estradiol, Estriol, and Progesterone) Safer or More Efficacious than Commonly Used Synthetic Versions in Hormone Replacement Therapy?," Postgraduate Medicine, 121(1): 73-85 (2009).
Honjo et al., "Progestins and estrogens and Alzheimer's disease,"Journal of Steroid Biochemistry & Molecular Biology, 93:305-308 (2005).
MacKenzie-Graham et al., "Estriol-mediated neuroprotection in multiple sclerosis localized by voxel-based morphometry." Brain and behavior: e01086 (2010).
Prometrium® Label, progesterone, USP.
Reed et al., "The Normal Menstrual Cycle and the Control of Ovulation," Europepmc.ord, 1-26 (2018).
Rosti et al., "The PASAT performance among patients with multiple sclerosis: analyses of responding patterns using different scoring methods," Multiple Sclerosis, 12:586-593 (2006).
Schiff et al., "Effect of Estriol Administration on the Hypogonadal Woman," Fertility and Sterility, 30(3):278-282 (1978).
Schiff et al., "Plasma estriol and its conjugates following oral and vaginal administration of estriol to postmenopausal women: Correlations with gonadotropin levels," Am J Obstet Gynecol, 138(8):1137-1141 (1980).
Sicotte et al., "Treatment of Multiple Sclerosis with Pregnancy Hormone Estriol," Ann Neurol, 52:421-428 (2002).
Tiwari-Woodruff et al., "Neuroprotective and anti-inflammatory effects of estrogen receptor ligand treatment in mice," Journal of Neurological Sciences, 286:81-85 (2009).

\* cited by examiner

A

B

Placebo + GA

Estriol + GA

Placebo + GA vs. Estriol + GA

ESTROGEN THERAPY FOR BRAIN GRAY MATTER ATROPHY AND ASSOCIATED DISABILITY

PRIORITY CLAIM

This application is a § 371 national-stage application based on PCT Application PCT/US15/047906, filed Sep. 1, 2015, which claims priority to U.S. Provisional Patent Application No. 62/044,757, filed on Sep. 2, 2014, which is hereby incorporated by reference in its entirety.

STATEMENT OF GOVERNMENT SUPPORT

This invention was made with government support under Grant Number NS051591, awarded by the National Institutes of Health. The government has certain rights in the invention.

BACKGROUND

Multiple sclerosis (MS) is a chronic, often debilitating disease affecting the central nervous system (CNS, brain and spinal cord). MS affects more than 1 million people worldwide and is the most common neurological disease among young adults, particularly women. The exact cause of MS is still unknown. MS is an autoimmune disease in which myelin sheaths surrounding neuronal axons are destroyed. This condition can cause weakness, impaired vision, loss of balance, poor muscle coordination, and cognitive difficulties.

While MS causes multifocal white matter lesions that are readily visible on magnetic resonance imaging (MRI), multifocal gray matter lesions, though less conspicuous, are present as well. Gray matter involvement begins early in MS and is mostly characterized by volume loss, i.e., cortical thinning and subcortical atrophy. Brain atrophy, and in particular, brain gray matter atrophy, is now associated with disability in MS. Shiee N et al. *PLoS ONE* 7(5): e37049 (2012).

MS takes several forms, with new symptoms either occurring in isolated attacks (relapsing forms) or building up over time (progressive forms). Between attacks, symptoms may disappear completely; however, permanent neurological problems often occur, especially as the disease advances.

In 1996, the United States National Multiple Sclerosis Society described four clinical subtypes of MS: (i) relapsing-remitting; (ii) secondary-progressive; (iii) primary-progressive; and (iv) progressive-relapsing.

Relapsing-remitting MS is characterized by unpredictable relapses followed by periods of months to years of relative quiet (remission) with no new signs of disease activity. Deficits that occur during attacks may either resolve or leave sequelae, the latter in about 40% of attacks and being more common the longer a person has had the disease. This describes the initial course of 80% of individuals with MS. When deficits always resolve between attacks, this is sometimes referred to as benign MS, although people will still build up some degree of disability in the long term. On the other hand, the term malignant multiple sclerosis is used to describe people with MS having reached significant level of disability in a short period of time. The relapsing-remitting subtype usually begins with a clinically isolated syndrome (CIS). In CIS, a person has an attack suggestive of demyelination but does not fulfill the criteria for multiple sclerosis; 30 to 70% of persons experiencing CIS go on to develop MS.

Secondary-progressive MS occurs in around 65% of those with initial relapsing-remitting MS, who eventually have progressive neurologic decline between acute attacks without any definite periods of remission. Occasional relapses and minor remissions may appear. The median length of time between disease onset and conversion from relapsing-remitting to secondary progressive MS is 19 years.

Primary-progressive MS occurs in approximately 10-20% of individuals, with no remission after the initial symptoms. It is characterized by progression of disability from onset, with no, or only occasional and minor, remissions and improvements. The usual age of onset for the primary progressive subtype is later than of the relapsing-remitting subtype, but similar to the age that secondary-progressive MS usually transitions from relapsing-remitting MS, around 40 years of age.

Progressive-relapsing MS describes those individuals who, from onset, have a steady neurologic decline but also have clear superimposed attacks. This is the least common of all subtypes.

Currently the following agents are approved by the U.S. Food and Drug Administration (FDA) to reduce disease activity and disease progression for many people with relapsing forms of MS, including relapsing-remitting MS, as well as secondary-progressive and progressive-relapsing MS in those people who continue to have relapses: dimethyl fumarate (Tecfidera®; BG-12), fingolimod (Gilenya®), glatiramer acetate (Copaxone®), interferon beta-1a (Avonex® and Rebif®), interferon beta-1b (Betaseron® and Extavia®), mitoxantrone (Novantrone®), natalizumab (Tysabri®), and teriflunomide (Aubagio®). Among drugs under development for the treatment of MS is anti-LINGO-1 (BIIB033, Biogen-Idec), a fully human monoclonal antibody which targets LINGO-1, a protein expressed selectively in the CNS that is known to negatively regulate axonal myelination and axonal regeneration. However, many of these therapies fail to successfully treat all patients or all symptoms in treated patients, and many of these therapies are associated with undesirable side effects. Accordingly, alternative therapies are needed.

SUMMARY

An aspect of the invention is a method of slowing or halting gray matter atrophy in a neurodegenerative disease patient, comprising administering to the patient an estrogen.

An aspect of the invention is a method of treating neurodegenerative disease in a patient having substantial brain gray matter atrophy, comprising administering to the patient an effective amount of an estrogen. In some aspects, the present invention relates to a method of treating or preventing a neurodegenerative disease, in a patient having greater than about 0.1% brain gray matter loss per annum, comprising administering to the patient an effective amount of an estrogen.

An aspect of the invention is a method of treating a neurodegenerative disease in a patient having a loss of brain gray matter of greater than about 0.3% in a period of at least about 6 months, comprising administering to the patient an effective amount of an estrogen.

An aspect of the invention is a method of treating a neurodegenerative disease in a patient having memory loss over a period of at least about 6 months, comprising administering to the patient an effective amount of an estrogen.

An aspect of the invention is a method of treating a neurodegenerative disease in a patient who is non-responsive to treatment with a multiple sclerosis therapy, comprising administering to the patient an effective amount of an estrogen, wherein the patient is classified as non-responsive based on a substantial loss of brain gray matter volume during treatment with the first treatment agent.

An aspect of the invention is a method of treating a neurodegenerative disease in a patient who is non-responsive to treatment with a multiple sclerosis therapy, comprising administering to the patient an effective amount of an estrogen, wherein the patient is classified as non-responsive based on a substantial loss of memory during treatment with the first treatment agent.

An aspect of the invention is a method of reversing gray matter atrophy in a neurodegenerative disease patient, comprising administering to the patient an estrogen.

An aspect of the invention is a method of slowing or halting progression of disability in a neurodegenerative disease patient, comprising administering to the patient an estrogen.

An aspect of the invention is a method of reversing progression of disability in a neurodegenerative disease patient, comprising administering to the patient an estrogen.

An aspect of the invention is a method of preventing progression of a neurodegenerative disease, comprising administering to a patient presenting with brain gray matter atrophy an effective amount of an estrogen.

An aspect of the invention is a method of slowing or halting progression of memory loss in a neurodegenerative disease patient, comprising administering to the patient an estrogen.

An aspect of the invention is a method of reversing progression of memory loss in a neurodegenerative disease patient, comprising administering to the patient an estrogen.

An aspect of the invention is a method of preventing progression of a neurodegenerative disease, comprising administering to a patient presenting with memory loss an effective amount of an estrogen.

An aspect of the invention is method of treating and/or slowing progression of a neurodegenerative disease, comprising: evaluating a patient's brain gray matter; and administering an effective amount of an estrogen to a patient suffering from brain gray matter atrophy.

An aspect of the invention is method of treating and/or slowing progression of a neurodegenerative disease, comprising: evaluating a patient's memory and administering an effective amount of an estrogen to a patient suffering from memory loss.

In certain embodiments, the estrogen is selected from estriol (E3), estradiol (E2), estrone (E1), an ester thereof, a pharmaceutically acceptable salt of an ester thereof, and any combination thereof.

In certain embodiments, the estrogen is estriol.

In certain embodiments, the method further comprises administering to the patient an immunotherapeutic agent, wherein the immunotherapeutic agent is neither an estrogen nor a progestogen, e.g., an immunotherapeutic agent selected from interferon-beta 1a, interferon-beta 1b, glatiramer acetate, natalizumab, mitoxantrone, fingolimod, teriflunomide, and dimethyl fumarate.

Another aspect of the invention is a method of treating a neurodegenerative disease, comprising
administering to a subject in need thereof a treatment regimen;
assessing a change in total (whole) brain gray matter volume of the subject over a period of time; and
changing the treatment regimen if the total (whole) brain gray matter volume decreases by at least about 0.3 percent between a first assessment and a second assessment.

In certain embodiments, the second assessment occurs at least about 6 months after the first assessment, such as about six months after the first assessment. In other embodiments, the second assessment occurs about one year after the first assessment, and the treatment regimen is changed if the total (whole) brain gray matter volume decreases by at least about 0.6 percent between the first assessment and the second assessment. In yet other embodiments, the second assessment occurs about two years after the first assessment, and the treatment regimen is changed if the total (whole) brain gray matter volume decreases by at least about 1.0 percent between the first assessment and the second assessment.

In certain embodiments, the assessing comprises performing brain magnetic resonance imaging (MRI).

In certain embodiments, the assessing consists of performing brain magnetic resonance imaging (MRI).

In certain embodiments, gray matter is assessed using an imaging technique or a surrogate marker.

In certain embodiments, the second assessment is performed at least about one year after the first assessment.

In certain embodiments, the second assessment is performed about one year after the first assessment.

In certain embodiments, the treatment regimen comprises estrogen, wherein the estrogen is selected from estriol (E3), estradiol (E2), estrone (E1), an ester thereof, a pharmaceutically acceptable salt of an ester thereof, and any combination thereof.

In certain embodiments, the estrogen is estriol.

In certain embodiments, the treatment regimen further comprises administering to the subject an immunotherapeutic agent.

In certain embodiments, the immunotherapeutic agent is selected from interferon-beta 1a, interferon-beta 1b, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

An aspect of the invention is a method of treating a neurodegenerative disease, comprising
administering to a human subject in need thereof a treatment regimen;
assessing a change in gray matter volume of at least two brain regions of the subject over a period of time; and
changing the treatment regimen if the gray matter volume of the at least two brain regions decreases by at least about 0.3 percent between a first assessment and a second assessment. In certain embodiments, the second assessment occurs at least about 6 months after the first assessment, such as about six months after the first assessment. In other embodiments, the second assessment occurs about one year after the first assessment, and the treatment regimen is changed if the gray matter volume of the at least two brain regions decreases by at least about 0.6 percent between the first assessment and the second assessment. In yet other embodiments, the second assessment occurs about two years after the first assessment, and the treatment regimen is changed if the gray matter volume of the at least two brain regions decreases by at least about 1.0 percent between the first assessment and the second assessment.

In certain embodiments, the assessing comprises performing brain magnetic resonance imaging (MRI).

In certain embodiments, the assessing consists of performing brain magnetic resonance imaging (MRI).

An aspect of the invention is a method of treating a neurodegenerative disease, comprising: administering to a human subject in need thereof a treatment regimen; assessing a change in memory over a period of time; and changing the treatment regimen if the memory of the subject declines between a first assessment and a second assessment. In certain embodiments, the second assessment occurs at least about 6 months after the first assessment, such as about six months after the first assessment. In other embodiments, the second assessment occurs about one year after the first assessment, and the treatment regimen is changed if the memory of the subject declines between the first assessment and the second assessment. In yet other embodiments, the second assessment occurs about two years after the first assessment, and the treatment regimen is changed if the memory of the subject declines between the first assessment and the second assessment.

In certain embodiments, the second assessment is performed at least about one year after the first assessment.

In certain embodiments, the second assessment is performed about one year after the first assessment.

In certain embodiments, the treatment regimen comprises estrogen, wherein the estrogen is selected from estriol (E3), estradiol (E2), estrone (E1), an ester thereof, a pharmaceutically acceptable salt of an ester thereof, and any combination thereof.

In certain embodiments, the estrogen is estriol.

In certain embodiments, the treatment regimen further comprises administering to the subject an immunotherapeutic agent.

In certain embodiments, the immunotherapeutic agent is selected from interferon-beta 1a, interferon-beta 1b, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

In certain embodiments, the neurodegenerative disease is multiple sclerosis.

In certain embodiments, the neurodegenerative disease is relapsing-remitting multiple sclerosis.

In certain embodiments, the neurodegenerative disease is secondary-progressive multiple sclerosis.

In certain embodiments, the neurodegenerative disease is primary-progressive multiple sclerosis.

In certain embodiments, the neurodegenerative disease is progressive-relapsing multiple sclerosis.

In certain embodiments, the neurodegenerative disease is clinically isolated syndrome (CIS).

In certain embodiments, the subject is a subject being treated with an immunotherapeutic agent yet experiencing a relapse and/or progression of the multiple sclerosis.

An aspect of the invention is a method of treating multiple sclerosis in a patient having a loss of brain gray matter of greater than about 0.3% in a period of at least about 6 months, comprising administering to the patient about 8 mg of estriol daily.

An aspect of the invention is a method of treating multiple sclerosis in a patient having memory loss over a period of at least about 6 months, comprising administering to the patient about 8 mg of estriol daily.

Although the methods disclosed throughout the specification and claims are useful for treating multiple sclerosis in its various forms and stages, these methods can also be applied the treatment of other neurodegenerative diseases, such as, by way of illustration, Alzheimer's disease, Parkinson's disease, stroke, amyotrophic lateral sclerosis, cerebellar ataxia, frontotemporal dementia, prion disease, Huntington's Disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, trauma-induced brain damage, and spinal cord injury. In certain preferred embodiments, the neurodegenerative disease is multiple sclerosis. In preferred embodiments, the patient is a woman. In some embodiments, the patient is a premenopausal or perimenopausal woman. In other embodiments, the patient is a postmenopausal woman.

DETAILED DESCRIPTION

Figure 1:
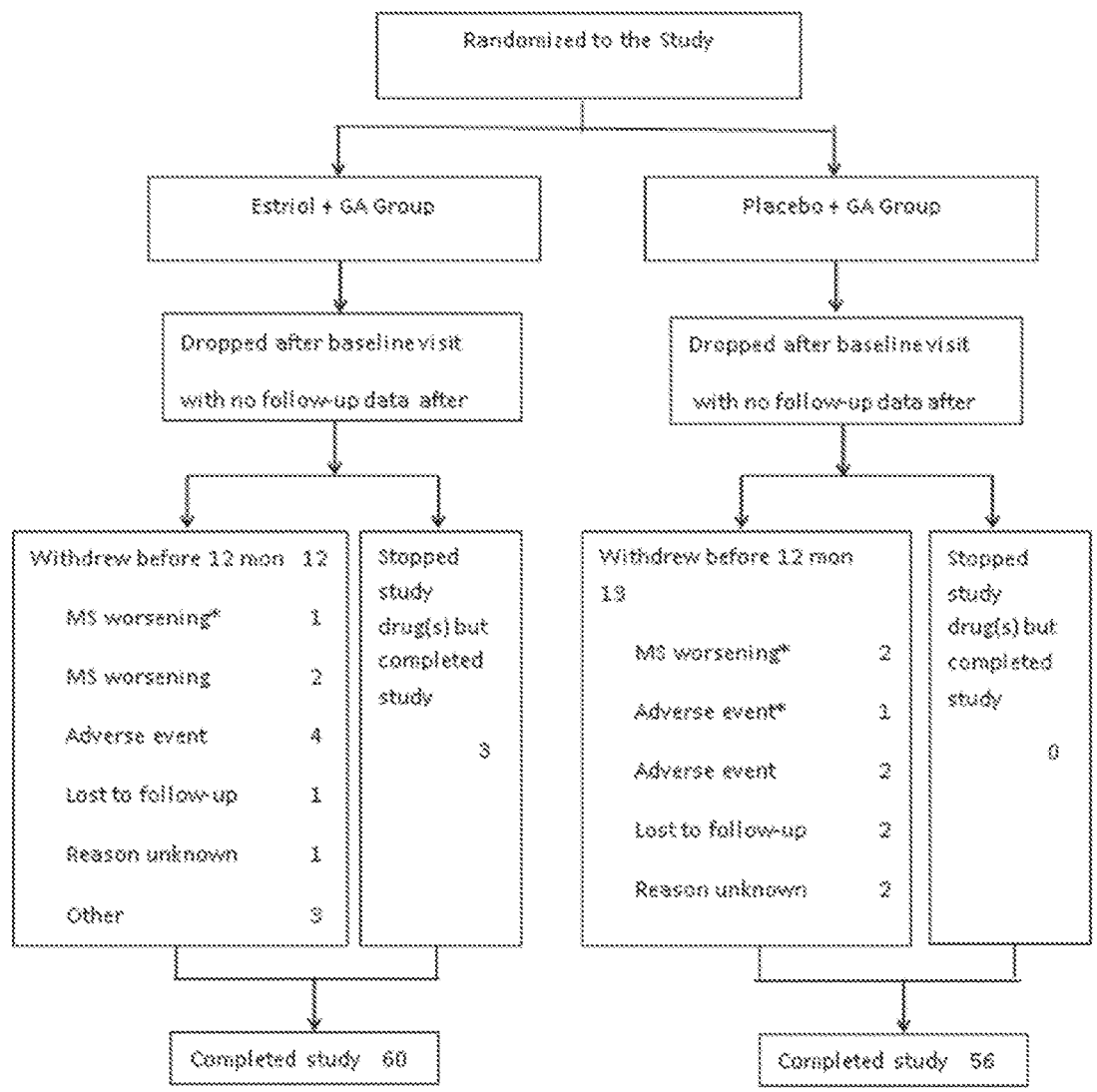
FIG. 1 includes two panels, identified as panels (A) and (B). Panel A shows the disposition of subjects enrolled in a clinical trial of estriol for treating multiple sclerosis. Panel B shows the study design. "Taper" indicates a period of reduction of either estriol or placebo over the course of 4 weeks at end of study, after month 24 clinic visit. Specifically, the dose of estriol was reduced by half (from 8 mg to 4 mg) for 2 weeks, then reduced by half again (from 4 mg to 2 mg) for 2 weeks, then discontinued. "x" indicates the administration of a progestin (0.7 mg norethindrone) orally each day for 2 weeks every three months, beginning at study month 6. "o" indicates the administration of a placebo for the progestin orally each day for 2 weeks every three months, beginning at study month 6.
Figure 1:
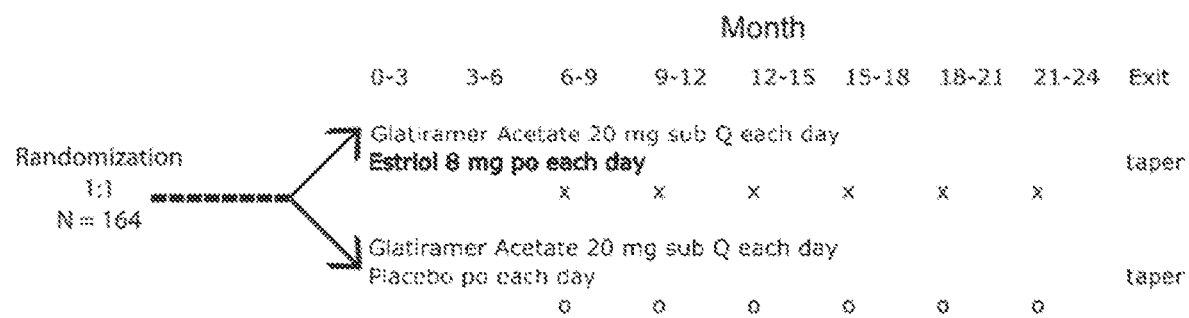

Approximately 50% of people diagnosed with multiple sclerosis (MS) will develop problems with cognition. Currently, there are no FDA-approved treatments targeting cognitive function in MS. Multiple sclerosis relapses are known to be significantly decreased by approximately 80% during late pregnancy. This disease improvement may be due to estriol, an estrogen unique to pregnancy. Estriol blood levels go from undetectable levels prior to pregnancy, increase during pregnancy and reach highest levels during late pregnancy. Further, estrogen treatment has been shown to have favorable effects on cognition in animal models of other neurological diseases.

There is an unmet need for a treatment to halt disability in MS. Brain gray matter (GM) atrophy is a biomarker for disability in MS. A treatment that can halt GM atrophy in MS would be promising to halt disability in MS. This GM biomarker could be used in trials to screen drugs aiming to halt disability in MS. This GM biomarker could also be used to follow patients to predict which will have future worsening of disability and hence may need to change their treatment regimen to start estriol treatment (either as a monotherapy in untreated or as an add-on treatment in those on standard MS treatment) to prevent further decline from occurring or to slow further decline. Also, this GM biomarker could also be used to identify patients in early stages of disease and optionally direct the use of treatment methods described herein. Further, this GM biomarker could also be used to identify patients who have aggressive (e.g. non-responsive to standard treatments) or late-stage forms of disease and optionally direct the use of treatment methods described herein.

The invention is based, in part, on the surprising discovery by the inventor that an estrogen, at least in combination with a standard treatment for MS, dramatically slows, halts, and even reverses gray matter atrophy in MS. In accordance with the invention, estrogen is also believed to slow, halt, and even reverse progression of disability in MS and other neurodegenerative diseases.

As will be described in greater detail below, the estrogen can be used in combination with certain immunotherapeutic agents, for example, disease-modifying therapeutics (DMTs) useful in the treatment MS.

Alternatively or in addition, as will be described in greater detail below, the estrogen can be used in combination with a progestogen, for example where the estrogen is administered continuously whereas the progestogen is administered from time to time.

An aspect of the invention is a method of slowing or halting gray matter atrophy in a neurodegenerative disease patient, comprising administering to the patient an estrogen.

An aspect of the invention is a method of treating neurodegenerative disease in a patient having substantial brain gray matter atrophy, comprising administering to the patient an effective amount of an estrogen. In some aspects, the present invention relates to a method of treating or preventing a neurodegenerative disease, in a patient having greater than about 0.1% brain gray matter loss per annum (e.g., about 0.2%, or about 0.3%, or about 0.4%, or about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0% brain gray matter loss per annum), comprising administering to the patient an effective amount of an estrogen.

An aspect of the invention is a method of treating a neurodegenerative disease, in a patient having a loss of brain gray matter of greater than about 0.3% in a period of at least about 6 months (e.g., about 0.4%, or about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0 in a period of about 6 months, or about 12 months, or about 18 months, or about 24 months), comprising administering to the patient an effective amount of an estrogen.

An aspect of the invention is a method of treating a neurodegenerative disease, in a patient having memory loss over a period of at least about 6 months (e.g., a period of about 6 months, or about 12 months, or about 18 months, or about 24 months), comprising administering to the patient an effective amount of an estrogen.

The terms "substantial brain gray matter atrophy" and "substantial loss of brain gray matter volume" as used herein, refers to a patient having greater than about 0.5% brain gray matter loss per annum (e.g., about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0% brain gray matter loss per annum). For example, "substantial brain gray matter atrophy" and "substantial loss of brain gray matter volume" may refer to a patient having a loss of brain gray matter of greater than about 0.3% in a period of at least about 6 months (e.g., about 0.4%, or about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0 in a period of about 6 months, or about 12 months, or about 18 months, or about 24 months). The amount of gray matter loss may be determined, for example, by using an imaging technique or surrogate marker.

An aspect of the invention is a method of treating a neurodegenerative disease in a patient who is non-responsive to treatment with a multiple sclerosis therapy (e.g., one or more of dimethyl fumarate (Tecfidera®; BG-12), fingolimod (Gilenya®), glatiramer acetate (Copaxone®), interferon beta-1a (e.g., Avonex® and Rebif®), interferon beta-1b (e.g., Betaseron® and Extavia®), mitoxantrone (Novantrone®), natalizumab (Tysabri®), teriflunomide (Aubagio®) and anti-LINGO-1 antibody (BIIB033, Biogen-Idec), comprising administering to the patient an effective amount of an estrogen, wherein the patient is classified as non-responsive based on a substantial loss of brain gray matter volume during treatment with the first treatment agent.

An aspect of the invention is a method of treating multiple sclerosis in a patient having a loss of brain gray matter of greater than about 0.3% in a period of at least about 6 months, comprising administering to the patient about 8 mg of estriol daily.

An aspect of the invention is a method of treating multiple sclerosis in a patient having memory loss over a period of at least about 6 months, comprising administering to the patient about 8 mg of estriol daily.

An aspect of the invention is a method of reversing gray matter atrophy in a neurodegenerative disease patient, comprising administering to the patient an estrogen.

An aspect of the invention is a method of slowing or halting progression of disability in a neurodegenerative disease patient, comprising administering to the patient an estrogen.

An aspect of the invention is a method of reversing memory loss in a neurodegenerative disease patient, comprising administering to the patient an estrogen.

An aspect of the invention is a method of slowing or halting memory loss in a neurodegenerative disease patient, comprising administering to the patient an estrogen.

An aspect of the invention is a method of reversing progression of disability in a neurodegenerative disease patient, comprising administering to the patient an estrogen.

An aspect of the invention is a method of preventing progression of a neurodegenerative disease, comprising administering to a patient presenting with brain gray matter atrophy an effective amount of an estrogen.

An aspect of the invention is a method of preventing progression of a neurodegenerative disease, comprising administering to a patient presenting with memory loss an effective amount of an estrogen.

An aspect of the invention is method of treating and/or slowing progression of a neurodegenerative disease, comprising: evaluating a patient's brain gray matter; and administering an effective amount of an estrogen to a patient suffering from brain gray matter atrophy.

An aspect of the invention is method of treating and/or slowing progression of a neurodegenerative disease, comprising: evaluating a patient's memory; and administering an effective amount of an estrogen to a patient suffering from memory loss.

In certain embodiments, the neurodegenerative disease is Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, trauma-induced brain damage, or spinal cord injury.

In certain embodiments, the neurodegenerative disease is Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, or trauma-induced brain damage.

In certain embodiments, the neurodegenerative disease is multiple sclerosis.

In certain embodiments, the neurodegenerative disease is clinically isolated syndrome (CIS).

In certain embodiments, the neurodegenerative disease is relapsing-remitting multiple sclerosis.

In certain embodiments, the neurodegenerative disease is secondary-progressive multiple sclerosis.

In certain embodiments, the neurodegenerative disease is primary-progressive multiple sclerosis.

In certain embodiments, the neurodegenerative disease is progressive-relapsing multiple sclerosis.

The term "estrogen" as used herein refers to any biologically active form of estrogen or precursor thereof. The term "estrogen" thus embraces naturally occurring, synthetic, and semi-synthetic forms of estrogen, and biologically active, pharmaceutically acceptable salts and esters thereof. In certain embodiments, estrogen is selected from estriol (E3), estradiol (E2), estrone (E1), an ester thereof, a pharmaceutically acceptable salt of an ester thereof, and any combination of the foregoing. In certain embodiments, estrogen is estriol (E3) or an ester thereof, or a pharmaceutically acceptable salt of an ester thereof. For example, the estrogen can be estriol, estriol succinate, estriol dihexanoate, or estriol sulfate. In other embodiments, estrogen is estradiol (E2) or an ester thereof, or a pharmaceutically acceptable salt of an ester thereof, while in yet other embodiments, estrogen is estrone (E1) or an ester thereof, or a pharmaceutically acceptable salt of an ester thereof. In certain preferred embodiments, estrogen is estriol (E3). In certain embodiments, estrogen is estradiol (E2). In certain embodiments, estrogen is estrone (E1).

In certain embodiments, the estrogen is administered in a dose equal or equivalent to about 200 µg to about 20 mg estriol daily. For example, a dose of 2 to 4 mg of estriol is generally considered to be equivalent to 0.6 to 1.25 mg of conjugated estrogens or estrone. In certain embodiments, the estrogen is administered in a dose equal or equivalent to about 1 mg to about 10 mg estriol daily, preferably equal or equivalent to about 8 mg estriol daily. In most preferred embodiments, the estrogen is estriol administered in a dose of about 8 mg estriol daily.

In certain embodiments, the estrogen is formulated for oral administration, e.g., in a dose equal or equivalent to about 200 µg to about 20 mg estriol daily. For example, a dose of 2 to 4 mg of estriol is generally considered to be equivalent to 0.6 to 1.25 mg of conjugated estrogens or estrone. In certain embodiments, the estrogen is formulated for oral administration in a dose equal or equivalent to about 1 mg to about 10 mg estriol daily, preferably equal or equivalent to about 8 mg estriol daily. In most preferred embodiments, the estrogen is estriol formulated for oral administration in a dose of about 8 mg estriol daily.

In certain embodiments, the estrogen is orally administered in a dose equal or equivalent to about 200 µg to about 20 mg estriol daily. For example, a dose of 2 to 4 mg of estriol is generally considered to be equivalent to 0.6 to 1.25 mg of conjugated estrogens or estrone. In certain embodiments, the estrogen is orally administered in a dose equal or equivalent to about 1 mg to about 10 mg estriol daily, preferably equal or equivalent to about 8 mg estriol daily. In most preferred embodiments, the estrogen is estriol orally administered in a dose of about 8 mg estriol daily.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of MS. Alternatively, a therapeutically effective amount can refer to an amount sufficient to halt or slow the rate of brain gray matter atrophy that develops over a given time interval.

A therapeutically effective dose of the estrogen is, in some embodiments, one sufficient to raise the serum concentration above basal levels, and preferably to pregnancy levels or above pregnancy levels. In certain embodiments, the therapeutically effective dose of the estrogen is selected to result in serum levels in a patient equivalent to the steroid hormone level of that agent in women in the second or third trimester of pregnancy.

For example, during the normal female menstrual cycle estradiol levels are in the range of about 350 pg/mL serum. During pregnancy, there is about a 100-fold increase in the level of estradiol to about 10,000 to about 35,000 pg/mL serum. Correale et al., *J Immunol* 161:3365-74 (1998) and Gilmore et al., *J Immunol* 158:446-51 (1997). In contrast, estriol levels are undetectable during the menstrual cycle in the non-pregnant state. Estradiol levels rise progressively during pregnancy to levels from 3,000 to 30,000 pg/mL (3 to 30 ng/mL).

In one embodiment, where the estrogen is estriol, the dose is from about 4 to 16 milligrams daily, and more specifically, about 8 milligrams daily. In this embodiment, blood serum levels preferably reach at least about 2 ng/mL, may reach about 10 to about 35 ng/mL, or most preferably about 20-30 ng/mL. Sicotte et al. *Neurology* 56:A75 (2001). In some embodiments, estradiol (E2) levels would preferably reach at least about 2 ng/mL and most preferably about to 10-35 ng/mL. In some embodiments, estrone (E1) levels would preferably reach at least about 2 ng/mL and most preferably about 5-18 ng/mL. DeGroot et al., *Endocrinology* 3(9): 2171-223 (1994).

The dosage of the estrogen may be selected for an individual patient depending upon the route of administration, severity of disease, age and weight of the patient, other medications the patient is taking and other factors normally considered by the attending physician, when determining the individual regimen and dosage level as the most appropriate for a particular patient. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected. In vitro or in vivo assays can be employed to help identify optimal dosage ranges.

A therapeutically effective dose of the estrogen included in the dosage form is selected at least by considering the type of estrogen selected and the mode of administration. The dosage form may include the estrogen in combination with other inert ingredients, including adjuvants and pharmaceutically acceptable carriers for the facilitation of dosage to the patient as known to those skilled in the pharmaceutical arts. The dosage form may be any form suitable to cause the estrogen to enter into the tissues of the patient.

Pharmaceutically acceptable carriers can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can include, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. Any agent described herein, if desired, can also comprise minor amounts of wetting or emulsifying agents, or pH buffering agents.

In one embodiment, the dosage form of the estrogen is an oral preparation (liquid, tablet, capsule, caplet, or the like) which when consumed results in elevated serum estrogen levels. The oral preparation may comprise conventional carriers including diluents, binders, time-release agents, lubricants, and disintegrants.

In other embodiments of the invention, the dosage form of the estrogen may be provided in a topical preparation (lotion, cream, ointment, patch, or the like) for transdermal application.

Alternatively, the dosage form may be provided as a suppository or the like for transvaginal or transrectal application.

However, in other embodiments, the dosage form may also allow for preparations to be applied subcutaneously, intravenously, intramuscularly, or via the respiratory system.

In certain embodiments, the method includes the steps of administering to the patient, on a continuous basis throughout two or more consecutive treatment periods, a therapeutically effective amount of an estrogen; and administering to the patient, for only a portion of each treatment period, a therapeutically effective amount of a progestogen.

The term "progestogen" (also known as "gestagen") as used herein refers to any steroid hormone that binds to and activates a progesterone receptor, or a precursor thereof. The term "progestogen" thus embraces naturally occurring, synthetic, and semi-synthetic forms of progestogen, and biologically active, pharmaceutically acceptable salts and esters thereof.

In certain embodiments, the progestogen is selected from chlormadinone acetate, cyproterone acetate, desogestrel, dienogest, 5α-dihydroprogesterone, drospirenone (Yasmin®), ethinodiol acetate, ethynodiol diacetate, etonogestrel (Nexplanon®), gestodene, 17-hydroxyprogesterone, levonorgestrel (Alesse®), medroxyprogesterone acetate (17α-hydroxy-6α-methylprogesterone acetate; Provera®), megestrol, megestrol acetate (17α-acetoxy-6-dehydro-6-methylprogesterone), nestorone, nomegestrol acetate, norethindrone, norethindrone acetate (also known as norethisterone acetate), norethynodrel (Enovid®), norgestimate, norgestrel, progesterone, tanaproget, trimegestone, or a pharmaceutically acceptable salt of any of the foregoing, or any combination thereof.

In certain embodiments, progestogen is a progestin. The term "progestin" as used herein refers to a synthetic progestogen as defined herein. Examples of progestins include desogestrel, dienogest, drospirenone (Yasmin®), ethinodiol acetate, etonogestrel (Nexplanon®), gestodene, levonorgestrel (Alesse®), medroxyprogesterone acetate (Provera®), nestorone, nomegestrol acetate, norethindrone, norethindrone acetate, norethynodrel (Enovid®), norgestimate, norgestrel, and trimegestone.

In certain embodiments, the progestogen is selected from progesterone, 17-hydroxyprogesterone, 5α-dihydroprogesterone, norethindrone, norethindrone acetate (also known as norethisterone acetate), medroxyprogesterone acetate (17α-hydroxy-6α-methylprogesterone acetate), megestrol acetate (17α-acetoxy-6-dehydro-6-methylprogesterone), desogestrel, levonorgestrel, chlormadinone acetate, and cyproterone acetate, pharmaceutically acceptable salts of any of the foregoing, and any combination thereof. In certain embodiments, progestogen is selected from progesterone, 17-hydroxyprogesterone, 5α-dihydroprogesterone, norethindrone, norethindrone acetate (also known as norethisterone acetate), desogestrel, levonorgestrel, chlormadinone acetate, and cyproterone acetate, pharmaceutically acceptable salts and esters of any of the foregoing, and any combination thereof. In certain embodiments, progestogen is norethindrone or an ester thereof, or a pharmaceutically acceptable salt of an ester thereof, preferably norethindrone. In certain embodiments, progestogen is progesterone or an ester thereof, or a pharmaceutically acceptable salt of an ester thereof.

In certain embodiments, the progestogen is administered in a dose equal or equivalent to about 70 µg to about 7 mg norethindrone daily, such as about 100 µg to about 1 mg norethindrone daily, most preferably in a dose equal or equivalent to about 0.7 mg norethindrone daily. In certain preferred embodiments, the progestogen is norethindrone administered in a dose of 0.7 mg norethindrone daily.

In certain embodiments, the progestogen is formulated for oral administration, e.g., in a dose equal or equivalent to about 70 µg to about 7 mg norethindrone daily, such as about 100 µg to about 1 mg norethindrone daily, most preferably in a dose equal or equivalent to about 0.7 mg norethindrone daily. In certain preferred embodiments, the progestogen is norethindrone formulated for oral administration in a dose of 0.7 mg norethindrone daily.

In certain embodiments, the progestogen is orally administered in a dose equal or equivalent to about 70 µg to about 7 mg norethindrone daily, such as about 100 µg to about 1 mg norethindrone daily, most preferably in a dose equal or equivalent to about 0.7 mg (i.e., 700 µg) norethindrone daily. In certain preferred embodiments, the progestogen is norethindrone orally administered in a dose of 0.7 mg (i.e., 700 µg) norethindrone daily.

A therapeutically effective dose of the progestogen included in the dosage form can be selected at least by considering the type of progestogen selected and the mode of administration. The dosage form may include the progestogen in combination with other inert ingredients, including adjuvants and pharmaceutically acceptable carriers for the facilitation of dosage to the patient as known to those skilled in the pharmaceutical arts. The dosage form may be any form suitable to cause the progestogen to enter into the tissues of the patient.

In one embodiment, the dosage form of the progestogen is an oral preparation (liquid, tablet, capsule, caplet, or the like) which when consumed results in elevated serum progestogen levels. The oral preparation may comprise conventional carriers including diluents, binders, time-release agents, lubricants, and disintegrants.

In other embodiments of the invention, the dosage form of the progestogen may be provided in a topical preparation (lotion, cream, ointment, patch, or the like) for transdermal application.

Alternatively, the dosage form may be provided as a suppository or the like for transvaginal or transrectal application.

In certain embodiments, the estrogen is administered to the subject on a continuous basis throughout two or more consecutive treatment periods. In certain embodiments, a continuous basis means daily, i.e., on consecutive days. For example, estrogen administered orally to a subject on a daily basis throughout two or more consecutive treatment periods is deemed to be estrogen administered to the subject on a continuous basis throughout two or more consecutive treatment periods. Alternatively, estrogen administered transdermally to a subject on a daily basis throughout two or more consecutive treatment periods is deemed to be estrogen administered to the subject on a continuous basis throughout two or more consecutive treatment periods.

As used herein, a "treatment period" refers to a period of time during which a subject is receiving, on a continuous or daily basis, at least one therapeutic agent administered for the purpose of treating MS in the subject. In certain embodiments, each treatment period is at least 28 consecutive days. In certain embodiments, each treatment period is at least 56 consecutive days. In certain embodiments, each treatment period is at least 84 consecutive days. In certain embodiments, each treatment period is at least 112 consecutive days. In certain embodiments, each treatment period is at least 140 consecutive days. In certain embodiments, each treatment period is at least 168 consecutive days.

In certain embodiments, each treatment period is at least 4 consecutive weeks. In certain embodiments, each treatment period is at least 8 consecutive weeks. In certain embodiments, each treatment period is at least 12 consecutive weeks. In certain embodiments, each treatment period is at least 16 consecutive weeks. In certain embodiments, each treatment period is at least 20 consecutive weeks. In certain embodiments, each treatment period is at least 24 consecutive weeks.

In certain embodiments, each treatment period is at least one month. In certain embodiments, each treatment period is at least two consecutive months. In certain embodiments, each treatment period is at least three consecutive months. In certain embodiments, each treatment period is at least four consecutive months. In certain embodiments, each treatment period is at least five consecutive months. In certain embodiments, each treatment period is at least six consecutive months.

In certain embodiments, the progestogen is administered to the subject for only a portion of each treatment period. As used herein, "for only a portion of each treatment period" refers generally to a period of time that occurs during but is at least one day shorter than a treatment period. In a preferred embodiment, the phrase "for only a portion of each treatment period" refers generally to a period of consecutive days that occurs during but is at least one day shorter than a treatment period.

In certain embodiments, the portion of each treatment period is daily for all but at least 7 consecutive days of each treatment period. For example, if the treatment period is 28 days, in various embodiments the portion of such treatment period can be 1, 2, 3, 4, 5, 6, 7, 8, 9, 10, 1, 12, 13, 14, 15, 16, 17, 18, 19, 20, or 21 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, or 1 to 21.

In certain embodiments, the portion of each treatment period is daily for all but at least 14 consecutive days of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14.

In certain embodiments, the portion of each treatment period is daily for up to 7 consecutive days of each treatment period. For example, if the treatment period is 28 days, in various embodiments the portion of such treatment period can be 1, 2, 3, 4, 5, 6, or 7 consecutive days. For convenience, such portion can begin on day 1 of a treatment period, such that, for this example, the portion can encompass day 1 or days 1 to 2, 1 to 3, 1 to 4, 1 to 5, 1 to 6, or 1 to 7.

In certain embodiments, the portion of each treatment period is daily for up to 14 consecutive days of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14.

In certain embodiments, the portion of each treatment period is daily for all but at least half of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, or to 14.

Preferably the progestogen is administered to the subject for only a portion of each treatment period. During the remainder of the treatment period, in certain embodiments the subject can receive estrogen but neither progestogen nor a placebo in place of the progestogen. Alternatively, during the remainder of the treatment period, in certain embodiments the subject can receive both estrogen and a placebo in place of the progestogen.

In certain embodiments, the method further includes the steps of administering orally to the patient, on a continuous basis for 84 consecutive days (12 weeks), about 8 mg of estriol daily; and administering orally to the patient, for 14 consecutive days (2 weeks) of the 84 consecutive days (12 weeks), about 0.7 mg of progestogen daily. In certain embodiments, the 14 consecutive days (2 weeks) are the first 14 consecutive days (2 weeks) of the 84 consecutive days (12 weeks). That is, if the 84 consecutive days of estrogen administration are deemed to start on day 1, the progestogen is administered on days 1, 2, 3, 4, 5, 6, 7, 8, 9, 10, 11, 12, 13, and 14, and then stopped. In certain embodiments, the patient may then continue to receive estrogen but neither progestogen nor a placebo in place of the progestogen for the remaining 70 days. In other embodiments, the method further includes the step of administering to the patient a placebo in place of the progestogen on each of the days the progestogen is not administered to the patient. That is, the patient may then receive both estrogen and a placebo in place of the progestogen for the remaining 70 days.

In certain embodiments, the method further includes the steps of administering orally to the patient, on a continuous basis for 84 consecutive days (12 weeks), about 8 mg of estriol daily; and administering orally to the patient, for 14 consecutive days (2 weeks) of the 84 consecutive days (12 weeks), about 0.7 mg of norethindrone daily. In certain embodiments, the 14 consecutive days (2 weeks) are the first 14 consecutive days (2 weeks) of the 84 consecutive days (12 weeks). That is, if the 84 consecutive days of estrogen administration are deemed to start on day 1, the norethindrone is administered on days 1, 2, 3, 4, 5, 6, 7, 8, 9, 10, 11, 12, 13, and 14, and then stopped. In certain embodiments, the patient may then continue to receive estrogen but neither norethindrone nor a placebo in place of the norethindrone for the remaining 70 days. In other embodiments, the method further includes the step of administering to the patient a placebo in place of the norethindrone on each of the days the norethindrone is not administered to the patient. That is, the patient may then receive both estrogen and a placebo in place of the norethindrone for the remaining 70 days.

In certain embodiments, the method further comprises administering to the patient an immunotherapeutic agent.

The term "immunotherapeutic agent" as used herein refers to a compound with an objectively measurable effect on at least one aspect of the immune system or an immune response. In certain embodiments, the immunotherapeutic agent is immunosuppressive, i.e., it exerts an objectively measurable inhibitory effect on at least one aspect of the immune system or an immune response. In certain embodiments, the immunotherapeutic agent is anti-inflammatory. In certain embodiments, the immunotherapeutic agent is a small molecule (molecular weight less than or equal to about 1.5 kDa) pharmaceutical compound or composition. In certain embodiments, the immunotherapeutic agent is a biological compound or composition, e.g., an antibody, peptide, nucleic acid, etc.

In certain embodiments, the immunotherapeutic agent is not an estrogen. In certain embodiments, the immunotherapeutic agent is not a progestogen. Preferably, the immunotherapeutic agent is neither an estrogen nor a progestogen.

In certain embodiments, the immunotherapeutic agent is selected from dimethyl fumarate (Tecfidera®; BG-12), fingolimod (Gilenya®), glatiramer acetate (Copaxone®), for example "longer-lasting" 40 mg/ml or 20 mg/ml versions), interferon beta-1a (Avonex® or Rebif®), interferon beta-1b (Betaseron® or Extavia®)), mitoxantrone (Novantrone®), natalizumab (Tysabri®), and teriflunomide (Aubagio®), mycophenolate mofetil, paclitaxel, cyclosporine, corticosteroids (e.g., prednisone, methylprednisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®).

In certain embodiments, the immunotherapeutic agent is dimethyl fumarate (Tecfidera®; BG-12). In certain embodiments, the immunotherapeutic agent is fingolimod (Gilenya®). In certain embodiments, the immunotherapeutic agent is glatiramer acetate (Copaxone®). In certain embodiments, the immunotherapeutic agent is interferon beta-1a (Avonex® or Rebif®). In certain embodiments, the immunotherapeutic agent is interferon beta-1b (Betaseron® or Extavia®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is teriflunomide (Aubagio®).

In certain embodiments, the immunotherapeutic agent is an agent that reduces the activity of LINGO-1, e.g., anti-LINGO-1 antibody (BIIB033, Biogen-Idec).

In certain embodiments, treatment with the immunotherapeutic agent is initiated at the same time or about the same time as initiation of treatment with the estrogen.

In certain embodiments, the immunotherapeutic agent is selected from interferon-beta-1a, interferon-beta-1b, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

In certain embodiments, the immunotherapeutic agent is selected from interferon-beta 1a, interferon-beta 1b, glatiramer acetate, natalizumab, mitoxantrone, fingolimod, teriflunomide, and dimethyl fumarate.

In certain embodiments, the immunotherapeutic agent is glatiramer acetate.

An aspect of the invention is a method of treating a neurodegenerative disease, comprising
administering to a subject in need thereof a treatment regimen;
assessing a change in total (whole) brain gray matter volume of at least one brain region of the subject over a period of time; and
changing the treatment regimen if the total (whole) brain gray matter volume decreases by at least about 0.3 percent between a first assessment and a second assessment. In certain embodiments, the second assessment occurs at least about 6 months after the first assessment, such as about six months after the first assessment. In other embodiments, the second assessment occurs about one year after the first assessment, and the treatment regimen is changed if the total (whole) brain gray matter volume decreases by at least about 0.6 percent between the first assessment and the second assessment. In yet other embodiments, the second assessment occurs about two years after the first assessment, and the treatment regimen is changed if the total (whole) brain gray matter volume decreases by at least about 1.0 percent between the first assessment and the second assessment.

The term "subject" as used herein refers to a living mammal and may be interchangeably used with the term "patient". In certain embodiments, the subject is a human. Preferably, the human subject is female, such as a woman. In certain embodiments, the subject is a premenopausal or perimenopausal woman. In certain embodiments, the subject is a premenopausal woman. In certain embodiments, the subject is a perimenopausal woman. In certain embodiments, the subject is a postmenopausal woman.

In certain embodiments, a subject for a method as described herein has one or more of: experienced a first clinical episode, MRI features consistent with multiple sclerosis, an inadequate response to an alternate MS therapy (e.g., one or more of dimethyl fumarate (Tecfidera®; BG-12), fingolimod (Gilenya®), glatiramer acetate (Copaxone®), interferon beta-1a (e.g., Avonex® and Rebif®), interferon beta-1b (e.g., Betaseron® and Extavia®), mitoxantrone (Novantrone®), natalizumab (Tysabri®), teriflunomide (Aubagio®) and anti-LINGO-1 antibody (BIIB033, Biogen-Idec), and an inability to tolerate an alternate MS therapy (e.g., one or more of dimethyl fumarate (Tecfidera®; BG-12), fingolimod (Gilenya®), glatiramer acetate (Copaxone®), interferon beta-1a (Avonex® and Rebif®), interferon beta-1b (e.g., Betaseron® and Extavia®), mitoxantrone (Novantrone®), natalizumab (Tysabri®), teriflunomide (Aubagio®), and anti-LINGO-1 antibody (BIIB033, Biogen-Idec)).

In certain embodiments, the neurodegenerative disease is Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, trauma-induced brain damage, or spinal cord injury.

In certain embodiments, the neurodegenerative disease is Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, or trauma-induced brain damage.

In certain embodiments, the neurodegenerative disease is multiple sclerosis.

In certain embodiments, the neurodegenerative disease is clinically isolated syndrome (CIS).

In certain embodiments, the neurodegenerative disease is relapsing-remitting multiple sclerosis.

In certain embodiments, the neurodegenerative disease is secondary-progressive multiple sclerosis.

In certain embodiments, the neurodegenerative disease is primary-progressive multiple sclerosis.

In certain embodiments, the neurodegenerative disease is progressive-relapsing multiple sclerosis.

As used herein, in certain embodiments, "total (whole) brain gray matter" refers to the combined volume of all intracranial gray matter, i.e., rostral to the cervical spinal cord. As used herein, in certain embodiments, "total (whole)

brain gray matter" refers to the combined volume of gray matter of cerebral cortex, cerebellum, thalamus, caudate nucleus, and putamen.

In certain embodiments, the assessing comprises performing brain MRI.

In certain embodiments, the assessing consists of performing brain MRI.

In certain embodiments, the second assessment is performed about 2, 3, 4, 5, 6, 7, 8, 9, 10, or 11 months after the first assessment.

In certain embodiments, the second assessment is performed about 3 months after the first assessment.

In certain embodiments, the second assessment is performed about 4 months after the first assessment.

In certain embodiments, the second assessment is performed about 6 months after the first assessment.

In certain embodiments, the second assessment is performed at least about 6 months, at least about one year, at least about 18 months, or at least about two years after the first assessment.

In certain embodiments, the second assessment is performed at least about one year after the first assessment. For example, in various embodiments, the second assessment is performed about 12, 13, 14, 15, 16, 17, 18, 19, 20, 21, 22, 23, or 24 or more months after the first assessment. In various embodiments, the second assessment is performed about 2, 3, 4, 5, 6, 7, 8, 9, or 10 or more years after the first assessment.

In certain embodiments, the second assessment is performed about one year after the first assessment.

In certain embodiments, the second assessment is performed about two years after the first assessment.

In certain embodiments, the first assessment is performed before, at the same time as, or at about the same time as initiating the treatment regimen. In certain embodiments, the first assessment is performed after the treatment regimen is initiated.

The method includes the step of changing the treatment regimen if the total (whole) brain gray matter volume decreases by at least about 0.3 percent between a first assessment and a second assessment. In certain embodiments, the total (whole) brain gray matter volume decreases by 0.4, 0.5, 0.6, 0.7, 0.8, 0.9, 1.0, or greater than 1.0 percent between the first assessment and the second assessment.

As used herein, the phrase "treatment regimen" means a repeated or structured intervention made over a period of time with the intention of treating at least one manifestation of a disease or condition of a subject. A treatment regimen typically includes administration of at least one agent useful or believed to be useful in the treatment of the disease or condition. In certain embodiments, a treatment regimen includes administration of a single agent useful or believed to be useful in the treatment of the disease or condition. In certain embodiments, a treatment regimen includes administration of two agents useful or believed to be useful in the treatment of the disease or condition. In certain embodiments, a treatment regimen includes administration of three agents useful or believed to be useful in the treatment of the disease or condition.

As used herein, the phrase "changing the treatment regimen" means changing the amount or inclusion of at least one agent in the treatment regimen. For example, an agent can be increased, decreased, stopped, or replaced by another agent. In certain embodiments, a further agent can be added to the treatment regimen. For example, in certain embodiments, changing the treatment regimen involves adding estrogen, with or without progestogen, to the treatment regimen.

In certain embodiments, the treatment regimen does not comprise estrogen. In certain such embodiments, changing the treatment regimen comprises adding administration of estrogen to the treatment regimen. For example, if the treatment regimen comprises administering an immunotherapeutic agent but not estrogen, changing the treatment regimen may comprise adding administration of estrogen (e.g., according to any of the various protocols described herein) to the treatment regimen. In certain embodiments, the estrogen added to the treatment regimen is selected from estriol (E3), estradiol (E2), estrone (E1), an ester thereof, a pharmaceutically acceptable salt of an ester thereof, and any combination thereof, such as estriol (E3) or an ester thereof, or a pharmaceutically acceptable salt of an ester thereof, preferably estriol. In certain embodiments, the estrogen is administered continuously on a daily basis. In certain embodiments, the subject is female.

In certain embodiments, the treatment regimen consists of administering to the subject an immunotherapeutic agent. In certain embodiments, the immunotherapeutic agent is not an estrogen. In certain embodiments, the immunotherapeutic agent is not a progestogen. Preferably, the immunotherapeutic agent is neither an estrogen nor a progestogen. In certain embodiments, the immunotherapeutic agent is selected from dimethyl fumarate (Tecfidera®; BG-12), fingolimod (Gilenya®), glatiramer acetate (Copaxone®, for example "longer-lasting" 40 mg/ml or 20 mg/ml versions), interferon beta-1a (Avonex® or Rebif®), interferon beta-1b (Betaseron® or Extavia®), mitoxantrone (Novantrone®), natalizumab (Tysabri®), and teriflunomide (Aubagio®), mycophenolate mofetil, paclitaxel, cyclosporine, corticosteroids (e.g., prednisone, methylprednisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®). In certain embodiments, the immunotherapeutic agent is dimethyl fumarate (Tecfidera®; BG-12). In certain embodiments, the immunotherapeutic agent is fingolimod (Gilenya®). In certain embodiments, the immunotherapeutic agent is glatiramer acetate (Copaxone®). In certain embodiments, the immunotherapeutic agent is interferon beta-1a (Avonex® or Rebif®). In certain embodiments, the immunotherapeutic agent is interferon beta-1 b (Betaseron®) or Extavia®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is teriflunomide (Aubagio®). In certain embodiments, the immunotherapeutic agent is an agent that reduces the activity of LINGO-1, e.g., anti-LINGO-1 antibody (BIIB033, Biogen-Idec).

In certain embodiments, the treatment regimen comprises administering to the subject an estrogen. In certain embodiments, the estrogen is selected from estriol (E3), estradiol (E2), estrone (E1), an ester thereof, a pharmaceutically acceptable salt of an ester thereof, and any combination thereof.

In certain embodiments, estrogen is estriol (E3) or an ester thereof, or a pharmaceutically acceptable salt of an ester thereof. In certain embodiments, the estrogen is estriol.

In certain embodiments, the estrogen is administered continuously on a daily basis.

In certain embodiments, the subject is female.

In certain embodiments, the estrogen is administered orally in a dose equal or equivalent to about 200 µg to about 20 mg of estriol daily.

In certain embodiments, the estrogen is administered orally in a dose equal or equivalent to about 1 mg to about 10 mg of estriol daily.

In certain embodiments, the estrogen is administered orally in a dose equal or equivalent to about 8 mg of estriol daily.

In certain embodiments, adding administration of estrogen to the treatment regimen comprises administering to the subject, on a continuous basis throughout one or more consecutive treatment periods, a therapeutically effective amount of an estrogen; and administering to the subject, for only a portion of each treatment period, a therapeutically effective amount of a progestogen.

In certain embodiments, the treatment regimen continues for at least two treatment periods.

In certain embodiments, the progestogen is selected from chlormadinone acetate, cyproterone acetate, desogestrel, dienogest, 5α-dihydroprogesterone, drospirenone, ethinodiol acetate, ethynodiol diacetate, etonogestrel, gestodene, 17-hydroxyprogesterone, levonorgestrel, medroxyprogesterone acetate (17α-hydroxy-6α-methylprogesterone acetate), megestrol, megestrol acetate (7α-acetoxy-6-dehydro-6-methylprogesterone), nestorone, nomegestrol acetate, norethindrone, norethindrone acetate, norethynodrel, norgestimate, norgestrel, progesterone, tanaproget, trimegestone, pharmaceutically acceptable salts of any of the foregoing, and any combination thereof.

In certain embodiments, the progestogen is progesterone.

In certain embodiments, the progestogen is norethindrone.

In certain embodiments, each treatment period is at least 28 consecutive days.

In certain embodiments, each treatment period is at least 56 consecutive days.

In certain embodiments, each treatment period is at least 84 consecutive days.

In certain embodiments, each treatment period is at least 112 consecutive days.

In certain embodiments, each treatment period is at least 4 consecutive weeks.

In certain embodiments, each treatment period is at least 8 consecutive weeks.

In certain embodiments, each treatment period is at least 12 consecutive weeks.

In certain embodiments, each treatment period is at least 16 consecutive weeks.

In certain embodiments, each treatment period is at least one month.

In certain embodiments, each treatment period is at least two consecutive months.

In certain embodiments, each treatment period is at least three consecutive months.

In certain embodiments, each treatment period is at least four consecutive months.

In certain embodiments, the portion of each treatment period is daily for all but at least 7 consecutive days of each treatment period.

In certain embodiments, the portion of each treatment period is daily for all but at least 14 consecutive days of each treatment period.

In certain embodiments, the portion of each treatment period is daily for up to 7 consecutive days of each treatment period.

In certain embodiments, the portion of each treatment period is daily for up to 14 consecutive days of each treatment period.

In certain embodiments, the portion of each treatment period is daily for all but at least half of each treatment period.

In certain embodiments, the progestogen is administered orally in a dose equal or equivalent to about 70 µg to about 7 mg of norethindrone daily.

In certain embodiments, the progestogen is administered orally in a dose equal or equivalent to about 100 µg to about 1 mg of norethindrone daily.

In certain embodiments, the progestogen is administered orally in a dose equal or equivalent to about 700 µg of norethindrone daily.

In certain embodiments, the estrogen is administered orally in a dose equal or equivalent to about 200 µg to about 20 mg of estriol daily.

In certain embodiments, the estrogen is administered orally in a dose equal or equivalent to about 1 mg to about 10 mg of estriol daily.

In certain embodiments, the estrogen is administered orally in a dose equal or equivalent to about 8 mg of estriol daily.

In certain embodiments, the treatment regimen further comprises administering to the subject an immunotherapeutic agent.

In certain embodiments, the immunotherapeutic agent is immunosuppressive. In certain embodiments, the immunotherapeutic agent is anti-inflammatory. In certain embodiments, the immunotherapeutic agent is a small molecule (molecular weight less than or equal to about 1.5 kDa) pharmaceutical compound or composition. In certain embodiments, the immunotherapeutic agent is a biological compound or composition, e.g., an antibody, peptide, nucleic acid, etc.

In certain embodiments, the immunotherapeutic agent is not an estrogen. In certain embodiments, the immunotherapeutic agent is not a progestogen. Preferably, the immunotherapeutic agent is neither an estrogen nor a progestogen.

In certain embodiments, the immunotherapeutic agent is selected from dimethyl fumarate (Tecfidera®; BG-12), fingolimod (Gilenya®), glatiramer acetate (Copaxone®, for example "longer-lasting" 40 mg/ml or 20 mg/ml versions), interferon beta-1a (Avonex® or Rebif®), interferon beta-1b (Betaseron® or Extavia®), mitoxantrone (Novantrone®), natalizumab (Tysabri®), and teriflunomide (Aubagio®), mycophenolate mofetil, paclitaxel, cyclosporine, corticosteroids (e.g., prednisone, methylprednisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®).

In certain embodiments, the immunotherapeutic agent is dimethyl fumarate (Tecfidera®; BG-12). In certain embodiments, the immunotherapeutic agent is fingolimod (Gilenya®). In certain embodiments, the immunotherapeutic agent is glatiramer acetate (Copaxone®)). In certain embodiments, the immunotherapeutic agent is interferon beta-1a (Avonex® or Rebif®). In certain embodiments, the immunotherapeutic agent is interferon beta-1b (Betaseron® or Extavia®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is teriflunomide (Aubagio®)).

In certain embodiments, the immunotherapeutic agent is an agent that reduces the activity of LINGO-1, e.g., anti-LINGO-1 antibody (BIIB033, Biogen-Idec).

In certain embodiments, treatment with the immunotherapeutic agent is initiated at the same time or about the same time as initiation of treatment with the estrogen.

In certain embodiments, the immunotherapeutic agent is selected from interferon-beta 1a, interferon-beta 1b, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

In certain embodiments, the immunotherapeutic agent is selected from interferon-beta 1a, interferon-beta 1b, glatiramer acetate, natalizumab, mitoxantrone, fingolimod, teriflunomide, and dimethyl fumarate.

In certain embodiments, the immunotherapeutic agent is glatiramer acetate.

An aspect of the invention is a method of treating a neurodegenerative disease, comprising
administering to a human subject in need thereof a treatment regimen;
assessing a change in gray matter volume of at least two brain regions of the subject over a period of time; and
changing the treatment regimen if the gray matter volume of the at least two brain regions decreases by at least about 0.3 percent between a first assessment and a second assessment. In certain embodiments, the second assessment occurs at least about 6 months after the first assessment, such as about six months after the first assessment. In other embodiments, the second assessment occurs about one year after the first assessment, and the treatment regimen is changed if the gray matter volume of the at least two brain regions decreases by at least about 0.6 percent between the first assessment and the second assessment. In yet other embodiments, the second assessment occurs about two years after the first assessment, and the treatment regimen is changed if the gray matter volume of the at least two brain regions decreases by at least about 1.0 percent between the first assessment and the second assessment.

In certain embodiments, the neurodegenerative disease is Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, trauma-induced brain damage, or spinal cord injury.

In certain embodiments, the neurodegenerative disease is Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, or trauma-induced brain damage.

In certain embodiments, the neurodegenerative disease is multiple sclerosis.

In certain embodiments, the neurodegenerative disease is clinically isolated syndrome (CIS).

In certain embodiments, the neurodegenerative disease is relapsing-remitting multiple sclerosis.

In certain embodiments, the neurodegenerative disease is secondary-progressive multiple sclerosis.

In certain embodiments, the neurodegenerative disease is primary-progressive multiple sclerosis.

In certain embodiments, the neurodegenerative disease is progressive-relapsing multiple sclerosis.

In certain embodiments, the treatments described herein involve one or more of preventing disease progression, slowing of disease progression, reducing the number of disease relapses or clinical exacerbations, slowing memory loss, and slowing the accumulation of physical disability.

In certain embodiments, the assessing comprises performing brain MRI.

In certain embodiments, the assessing consists of performing brain MRI.

In certain embodiments, the at least two brain regions are selected from cerebral cortex, cerebellum, thalamus, caudate nucleus, putamen, and any combination thereof.

In certain embodiments, one of the at least two brain regions comprises cerebral cortex.

In certain embodiments, the second assessment is performed about 2, 3, 4, 5, 6, 7, 8, 9, 10, or 11 months after the first assessment.

In certain embodiments, the second assessment is performed about 3 months after the first assessment.

In certain embodiments, the second assessment is performed about 4 months after the first assessment.

In certain embodiments, the second assessment is performed about 6 months after the first assessment.

In certain embodiments, the second assessment is performed at least about 6 months, at least about one year, at least about 18 months, or at least about two years after the first assessment.

In certain embodiments, the second assessment is performed at least about one year after the first assessment. For example, in various embodiments, the second assessment is performed about 12, 13, 14, 15, 16, 17, 18, 19, 20, 21, 22, 23, or 24 or more months after the first assessment. In various embodiments, the second assessment is performed about 2, 3, 4, 5, 6, 7, 8, 9, or 10 or more years after the first assessment.

In certain embodiments, the second assessment is performed about one year after the first assessment.

In certain embodiments, the second assessment is performed about two years after the first assessment.

In certain embodiments, the first assessment is performed before, at the same time as, or at about the same time as initiating the treatment regimen. In certain embodiments, the first assessment is performed after the treatment regimen is initiated.

The method includes the step of changing the treatment regimen if the gray matter volume decreases by at least about 4 mL between a first assessment and a second assessment. In certain embodiments, the gray matter volume decreases by 4, 5, 6, 7, 8, 9, 10, or greater than 10 mL between the first assessment and the second assessment.

In certain embodiments, the treatment regimen does not comprise estrogen, and changing the treatment regimen comprises adding administration of estrogen (e.g., according to any of the various protocols described herein) to the treatment regimen. For example, if the treatment regimen comprises administering an immunotherapeutic agent but not estrogen, changing the treatment regimen may comprise adding administration of estrogen to the treatment regimen. In certain embodiments, the estrogen added to the treatment regimen is selected from estriol (E3), estradiol (E2), estrone (E1), an ester thereof, a pharmaceutically acceptable salt of an ester thereof, and any combination thereof, such as estriol (E3) or an ester thereof, or a pharmaceutically acceptable salt of an ester thereof, preferably estriol. In certain embodiments, the estrogen is administered continuously on a daily basis. In certain embodiments, the subject is female.

In certain embodiments, the treatment regimen consists of administering to the subject an immunotherapeutic agent. In certain embodiments, the immunotherapeutic agent is not an estrogen. In certain embodiments, the immunotherapeutic agent is not a progestogen. Preferably, the immunotherapeutic agent is neither an estrogen nor a progestogen. In certain embodiments, the immunotherapeutic agent is selected from dimethyl fumarate (Tecfidera®; BG-12), fingolimod (Gilenya®), glatiramer acetate (Copaxone®, for example "longer-lasting" 40 mg/ml or 20 mg/ml versions), interferon beta-1a (e.g., Avonex® or Rebif®), interferon beta-1b (e.g., Betaseron® or Extavia®), mitoxantrone (Novantrone®), natalizumab (Tysabri®), and teriflunomide (Aubagio®), mycophenolate mofetil, paclitaxel, cyclosporine, corticosteroids (e.g., prednisone, methylprednisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (e.g., Betaseron® or Extavia®), mitoxantrone (Novantrone®), natalizumab (Tysabri®), and teriflunomide (Aubagio®). In certain embodiments, the immunotherapeutic agent is dimethyl fumarate (Tecfidera®; BG-12). In certain embodiments, the immunotherapeutic agent is fingolimod (Gilenya®). In certain embodiments, the immunotherapeutic agent is glatiramer acetate (Copaxone®). In certain embodiments, the immunotherapeutic agent is interferon beta-1a (Avonex® or Rebif®). In certain embodiments, the immunotherapeutic agent is interferon beta-1b (e.g., Betaseron® or Extavia®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is teriflunomide (Aubagio®). In certain embodiments, the immunotherapeutic agent is an agent that reduces the activity of LINGO-1, e.g., anti-LINGO-1 antibody (BIIB033, Biogen-Idec).

In certain embodiments, the treatment regimen comprises administering to the subject an estrogen. In certain embodiments, the estrogen is selected from estriol (E3), estradiol (E2), estrone (E1), an ester thereof, a pharmaceutically acceptable salt of an ester thereof, and any combination thereof.

In certain embodiments, estrogen is estriol (E3) or an ester thereof, or a pharmaceutically acceptable salt of an ester thereof. In certain embodiments, the estrogen is estriol.

In certain embodiments, the estrogen is administered continuously on a daily basis.

In certain embodiments, the subject is female.

In certain embodiments, the estrogen is administered orally in a dose equal or equivalent to about 200 µg to about 20 mg of estriol daily.

In certain embodiments, the estrogen is administered orally in a dose equal or equivalent to about 1 mg to about 10 mg of estriol daily.

In certain embodiments, the estrogen is administered orally in a dose equal or equivalent to about 8 mg of estriol daily.

In certain embodiments, adding administration of estrogen to the treatment regimen comprises administering to the subject, on a continuous basis throughout one or more consecutive treatment periods, a therapeutically effective amount of an estrogen; and administering to the subject, for only a portion of each treatment period, a therapeutically effective amount of a progestogen.

In certain embodiments, the treatment regimen continues for at least two treatment periods.

In certain embodiments, the progestogen is selected from chlormadinone acetate, cyproterone acetate, desogestrel, dienogest, 5α-dihydroprogesterone, drospirenone, ethinodiol acetate, ethynodiol diacetate, etonogestrel, gestodene, 17-hydroxyprogesterone, levonorgestrel, medroxyprogesterone acetate (17α-hydroxy-6α-methylprogesterone acetate), megestrol, megestrol acetate (17α-acetoxy-6-dehydro-6-methylprogesterone), nestorone, nomegestrol acetate, norethindrone, norethindrone acetate, norethynodrel, norgestimate, norgestrel, progesterone, tanaproget, trimegestone, pharmaceutically acceptable salts of any of the foregoing, and any combination thereof.

In certain embodiments, the progestogen is progesterone.

In certain embodiments, the progestogen is norethindrone.

In certain embodiments, each treatment period is at least 28 consecutive days.

In certain embodiments, each treatment period is at least 56 consecutive days.

In certain embodiments, each treatment period is at least 84 consecutive days.

In certain embodiments, each treatment period is at least 112 consecutive days.

In certain embodiments, each treatment period is at least 4 consecutive weeks.

In certain embodiments, each treatment period is at least 8 consecutive weeks.

In certain embodiments, each treatment period is at least 12 consecutive weeks.

In certain embodiments, each treatment period is at least 16 consecutive weeks.

In certain embodiments, each treatment period is at least one month.

In certain embodiments, each treatment period is at least two consecutive months.

In certain embodiments, each treatment period is at least three consecutive months.

In certain embodiments, each treatment period is at least four consecutive months.

In certain embodiments, the portion of each treatment period is daily for all but at least 7 consecutive days of each treatment period.

In certain embodiments, the portion of each treatment period is daily for all but at least 14 consecutive days of each treatment period.

In certain embodiments, the portion of each treatment period is daily for up to 7 consecutive days of each treatment period.

In certain embodiments, the portion of each treatment period is daily for up to 14 consecutive days of each treatment period.

In certain embodiments, the portion of each treatment period is daily for all but at least half of each treatment period.

In certain embodiments, the progestogen is administered orally in a dose equal or equivalent to about 70 μg to about 7 mg of norethindrone daily.

In certain embodiments, the progestogen is administered orally in a dose equal or equivalent to about 100 μg to about 1 mg of norethindrone daily.

In certain embodiments, the progestogen is administered orally in a dose equal or equivalent to about 700 μg of norethindrone daily.

In certain embodiments, the estrogen is administered orally in a dose equal or equivalent to about 200 μg to about 20 mg of estriol daily.

In certain embodiments, the estrogen is administered orally in a dose equal or equivalent to about 1 mg to about 10 mg of estriol daily.

In certain embodiments, the estrogen is administered orally in a dose equal or equivalent to about 8 mg of estriol daily.

In certain embodiments, the treatment regimen further comprises administering to the subject an immunotherapeutic agent.

In certain embodiments, the immunotherapeutic agent is immunosuppressive. In certain embodiments, the immunotherapeutic agent is anti-inflammatory. In certain embodiments, the immunotherapeutic agent is a small molecule (molecular weight less than or equal to about 1.5 kDa) pharmaceutical compound or composition. In certain embodiments, the immunotherapeutic agent is a biological compound or composition, e.g., an antibody, peptide, nucleic acid, etc.

In certain embodiments, the immunotherapeutic agent is not an estrogen. In certain embodiments, the immunotherapeutic agent is not a progestogen. Preferably, the immunotherapeutic agent is neither an estrogen nor a progestogen.

In certain embodiments, the immunotherapeutic agent is selected from dimethyl fumarate (Tecfidera®; BG-12), fingolimod (Gilenya®), glatiramer acetate (Copaxone®, for example "longer-lasting" 40 mg/ml or 20 mg/ml versions), interferon beta-1a (Avonex® or Rebif®), interferon beta-1b (Betaseron® or Extavia®), mitoxantrone (Novantrone®), natalizumab (Tysabri®), and teriflunomide (Aubagio®), mycophenolate mofetil, paclitaxel, cyclosporine, corticosteroids (e.g., prednisone, methylprednisolone), azathioprine, cyclophosphamide, methotrexate, cladribine, 4-aminopyridine, and tizanidine. In certain embodiments, the immunotherapeutic agent is selected from dimethyl fumarate (Tecfidera®; BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®).

In certain embodiments, the immunotherapeutic agent is dimethyl fumarate (Tecfidera®; BG-12). In certain embodiments, the immunotherapeutic agent is fingolimod (Gilenya®). In certain embodiments, the immunotherapeutic agent is glatiramer acetate (Copaxone®)). In certain embodiments, the immunotherapeutic agent is interferon beta-1a (Avonex® or Rebif®). In certain embodiments, the immunotherapeutic agent is interferon beta-1b (Betaseron® or Extavia®). In certain embodiments, the immunotherapeutic agent is mitoxantrone (Novantrone®). In certain embodiments, the immunotherapeutic agent is natalizumab (Tysabri®). In certain embodiments, the immunotherapeutic agent is teriflunomide (Aubagio®).

In certain embodiments, the immunotherapeutic agent is an agent that reduces the activity of LINGO-1, e.g., anti-LINGO-1 antibody (BIIB033, Biogen-Idec).

In certain embodiments, treatment with the immunotherapeutic agent is initiated at the same time or about the same time as initiation of treatment with the estrogen.

The various methods disclosed herein can be methods for improving walking, vision, balance, cognition, memory, or other symptoms in a subject, such as a subject with multiple sclerosis, and/or methods for improving multiple sclerosis functional composite (MSFC), EDSS, or MSSS scores in a subject, such as a subject with multiple sclerosis. Thus, in certain embodiments, the methods of treatment disclosed herein include methods for improving disability in a patient, whereby the patient's disability score (as measured by either of these tests or another suitable test) after two years of therapy is at least about 10%, at least about 25%, at least about 40%, at least about 50%, or even at least about 60% higher relative to a control patient not receiving the estrogen/progestogen therapy (but otherwise receiving the same treatment as the estrogen-treated patient).

In various embodiments, the present methods treat or prevent one or more symptoms of a neurodegenerative disease (e.g. MS) including, by way of illustration: optic neuritis, diplopia, nystagmus, ocular dysmetria, internuclear opthalmoplegia, movement and sound phosphenes, afferent pupillary defect, paresis, monoparesis, paraparesis, hemiparesis, quadraparesis, plegia, paraplegia, hemiplegia, tetraplegia, quadriplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, L'Hermitte's sign, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgamy, frigidity, constipation, fecal urgency, fecal incontinence, depression, cognitive dysfunction, memory loss, dementia, mood swings, emotional lability, euphoria, bipolar syndrome, anxiety, aphasia, dysphasia, fatigue, Uhthoff's symptom, gastroesophageal reflux, and sleeping disorders.

Improvements in cognition outcomes associated with MS therapy, whether slowing of cognitive decline, stabilization of cognitive decline, or improvement of cognitive function, can be assessed using the PASAT (e.g., PASAT 2 or PASAT 3) or SDMT test, or alternatively the MS-COG test (see Erlanger et al., *J Neuro Sci* 340: 123-129 (2014)). Thus, in certain embodiments, the methods of treatment disclosed herein include methods for stabilizing or improving cognition in a patient, whereby the patient's cognition outcome after one year of therapy is at least about 10%, at least about 25%, at least about 40%, at least about 50%, or even at least about 60% higher relative to a control patient not receiving the estrogen/progestogen therapy (but otherwise receiving the same treatment as the estrogen-treated patient), e.g., as measured by any of the preceding tests.

Improvements in memory associated with MS therapy, whether slowing of memory loss, stabilization of memory loss, or improvement of memory, can be assessed using, for example, the 7/24 Spatial Recall Test. Thus, in certain embodiments, the methods of treatment disclosed herein include methods for stabilizing memory loss or improving memory in a patient, whereby the patient's memory after one year of therapy is at least about 10%, at least about 25%, at least about 30%, at least about 40%, at least about 45%, at least about 50%, or even at least about 60% higher relative to a control patient not receiving the estrogen/progestogen therapy (but otherwise receiving the same treatment as the estrogen-treated patient), e.g., as measured by the 7/24 Spatial Recall Test.

In some embodiments, substantial loss of memory refers to worsening performance on the 7/24 Spatial Recall Test or Delayed Recall Test. For example, a subject who scores less than 7 on the Spatial Recall Test or Delayed Recall Test has substantial memory loss. Additionally, a subject who scores a 7 on the 7/24 Spatial Recall Test or Delayed Recall Test on a first date followed by a score of 6 or less on a subsequent date has substantial loss of memory over the period of time defined by the first date and the subsequent date.

While the various methods disclosed herein are typically efficacious when administered without additional therapeutics, in certain embodiments, any of these methods further includes the step of administering to the subject an immunotherapeutic agent, wherein the immunotherapeutic agent is neither an estrogen nor a progestogen. That is, in certain embodiments the subject is administered, in addition to the estrogen, a second agent useful in the treatment of MS. In certain embodiments, the subject is administered, in addition to the estrogen and progestogen (or placebo), a third agent useful in the treatment of MS. Such agents useful in the treatment of MS are, in general, immunotherapeutic agents. At least in connection with MS, such agents are sometimes referred to as disease-modifying therapies or disease-modifying therapeutics (DMTs).

In certain embodiments, the subject is already receiving a disease-modifying therapeutic. In this circumstance, the subject can continue to receive the disease-modifying therapeutic while taking the estrogen, with and without the progestogen. Significantly, however, the dose of the disease-modifying therapeutic may be decreased when used in combination with the estrogen, with and without the progestogen. For example, a current standard dose for glatiramer acetate (Copaxone®) is 40 mg subcutaneously (s.c.) three times a week, or 20 mg s.c. daily. In conjunction with estrogen and progestogen in accordance with the invention, the dose for glatiramer acetate (Copaxone®) may be reduced by up to 50 percent or more, e.g., to 20 mg s.c. three times a week.

As another example, a current standard dose for fingolimod (Gilenya®) is 0.5 mg by mouth (p.o.) daily. In conjunction with estrogen and progestogen in accordance with the invention, the dose for fingolimod (Gilenya®) may be reduced by up to 50 percent or more, e.g., to 0.25 mg p.o. daily.

As another example, a current standard dose for dimethyl fumarate (Tecfidera®) is 240 mg p.o. daily. In conjunction with estrogen and progestogen in accordance with the invention, the dose for dimethyl fumarate (Tecfidera®) may be reduced by up to 50 percent or more, e.g., to 120 mg p.o. daily.

As yet another example, a current standard dose for interferon beta-1a (Avonex® or Rebif®) is 30 µg intramuscularly (i.m.) weekly (Avonex®) or 44 µg s.c. three days a week (Rebif®). In conjunction with estrogen and progestogen in accordance with the invention, the dose for Avonex® may be reduced to 15 µg i.m. weekly, and the dose for Rebif® may be reduced to 22 µg s.c. three days a week.

As yet another example, a current standard dose for interferon beta-1b (Betaseron® or Extavia®) is 0.25 mg s.c. every other day (Betaseron® or Extavia®). In conjunction with estrogen and progestogen in accordance with the invention, the dose for interferon beta-1b (Betaseron® or Extavia®) may be reduced to 0.125 mg s.c. every other day.

In certain embodiments, the subject is receiving an immunotherapeutic agent and experiencing a relapse or progression of the multiple sclerosis. For example, a subject may experience a relapse or progression while on a maintenance dose of a DMT. Such subject can then begin concurrent treatment with estrogen in accordance with any of the various methods disclosed herein, e.g., to reduce the frequency and/or severity of relapses or to slow progression of the disease (e.g., as determined by assessment of one or more of walking, vision, balance, cognition, memory, or other symptoms of the condition, e.g., as measured according to the Expanded Disability Severity Scale (EDSS) and/or the multiple sclerosis functional composite (MSFC)). Thus, the various embodiments of the methods disclosed herein can be methods for improving walking, vision, balance, cognition, memory, or other symptoms in a subject, such as a subject with multiple sclerosis, and/or methods for improving EDSS or MSFC scores in a subject, such as a subject with multiple sclerosis.

In certain embodiments, the subject is receiving an immunotherapeutic agent and experiencing a relapse of the multiple sclerosis. For example, a subject may experience a relapse while on a maintenance dose of a DMT. Such subject can then begin concurrent treatment with estrogen in accordance with a method of the present invention, e.g., to reduce the frequency and/or severity of relapses.

In certain embodiments, the subject is receiving an immunotherapeutic agent selected from interferon-beta 1a, interferon-beta 1b, glatiramer acetate, natalizumab, mitoxantrone, fingolimod, teriflunomide, and dimethyl fumarate during a ramp-up period for dose of the immunotherapeutic agent, e.g., the patient begins receiving the immunotherapeutic and the estrogen therapy at the same time or at about the same time (such as for patients who have not previously received treatments for their disease). Advantageously, estrogen induces a rapid onset of therapeutic effect on MS, while commonly an immunotherapeutic agent such as interferon-beta 1a, interferon-beta-1b, glatiramer acetate, natalizumab, mitoxantrone, fingolimod, teriflunomide, or dimethyl fumarate may take weeks to months to induce observable improvements on some or all symptoms.

In certain embodiments, the subject is receiving glatiramer acetate during a ramp-up period for dose of the glatiramer acetate. In other certain embodiments, the subject is not already receiving a disease-modifying therapeutic.

In certain embodiments, the estrogen and the progestogen are formulated separately from one another, e.g., the subject receives the estrogen as a single formulation and the progestogen as a separate formulation. For oral administration, a given dose of each formulation can comprise one or more pills, tablets, capsules, or the like (i.e., unit doses). For example, an 8 mg dose of estriol can be administered as four 2 mg capsules, and a 0.7 mg dose of norethindrone can be administered as a single capsule, though preferably each dose is administered in a single unit dose (e.g., one unit dose each for the estrogen and the progestogen).

In certain embodiments, e.g., where a placebo is administered with the estrogen on days when progestogen is not administered, the estrogen and the placebo are formulated separately from one another. For example, the subject is administered the estrogen as a single formulation and the placebo as a separate formulation. For oral administration, a given dose of each formulation can comprise one or more pills, tablets, capsules, or the like (i.e., unit doses). For example, an 8 mg dose of estriol can be administered as four 2 mg capsules, and a placebo can be administered as a single capsule.

When a given dose of any agent involves administration of more than a single unit dose, e.g., four 2 mg capsules of estriol, the individual unit doses can be administered at essentially the same time, or they can be administered at different times on a given day, provided the entire daily dose is administered within a single day. For example, four 2 mg capsules of estriol can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

When the estrogen and the progestogen are formulated separately, they can be administered essentially simultaneously, or they can be administered sequentially with respect to each other. For example, in one embodiment the subject is administered four 2 mg capsules of estriol and one 0.7 mg capsule of norethindrone essentially simultaneously. In another embodiment, the subject is administered estriol in divided doses, e.g., two 2 mg capsules twice daily, and the progestogen is administered essentially simultaneously with one of the divided doses of estriol. In yet another embodiment, the subject is administered estriol in divided doses, e.g., two 2 mg capsules twice daily, and the progestogen is administered at a separate time from either one of the divided doses of estriol.

Similarly, when the estrogen and the placebo are formulated separately, they can be administered essentially simultaneously, or they can be administered sequentially with respect to each other. For example, in one embodiment the subject is administered four 2 mg capsules of estriol and one placebo essentially simultaneously. In another embodiment, the subject is administered estriol in divided doses, e.g., two 2 mg capsules twice daily, and the placebo is administered essentially simultaneously with one of the divided doses of estriol. In yet another embodiment, the subject is administered estriol in divided doses, e.g., two 2 mg capsules twice daily, and the placebo is administered at a separate time from either one of the divided doses of estriol.

In certain embodiments, the estrogen and the progestogen are formulated together. For oral administration, a given dose of each component, formulated together, can comprise one or more pills, tablets, capsules, or the like (i.e., unit doses). For example, an 8 mg dose of estriol and a 0.7 mg dose of norethindrone can be coformulated and administered as four capsules, each containing 2 mg estriol and 0.0875 mg norethindrone, though preferably, where applicable, they are coformulated as one unit dose comprising both the estrogen and the progestogen.

In certain embodiments, e.g., where a placebo is administered with the estrogen on days when progestogen is not administered, the estrogen and the placebo are formulated together. For oral administration, a given dose of each component, formulated together, can comprise one or more pills, tablets, capsules, or the like (i.e., unit doses). For example, an 8 mg dose of estriol and a placebo can be coformulated and administered as four capsules, each containing 2 mg estriol and a suitable amount of placebo.

When a given dose of any coformulation of estriol and progestogen (or placebo) involves administration of more than a single unit dose, e.g., four capsules, each containing 2 mg estriol and 0.0875 mg norethindrone, the individual unit doses can be administered at essentially the same time, or they can be administered at different times on a given day, provided the entire daily dose is administered within a single day. For example, four capsules, each containing estriol and progestogen (or placebo) can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

Clinically and in various embodiments, MS can be assessed and monitored using any of a number of structural (anatomical) and functional tests, including, without limitation: magnetic resonance imaging (MRI); Paced Serial Addition Test (PASAT); symbol digit modalities test (SDMT); expanded disability status score (EDSS); multiple sclerosis functional composite (MSFC); 25-foot walk test; 9-hole peg test; low contrast visual acuity; MS Quality of Life; Modified Fatigue Impact Scale; Beck Depression Inventory; 7/24 Spatial Recall Test; Benton Forms F & G; Buschke Selective Reminding Test; Verbal Paired Associates; Word List Generation. Recently, the PASAT test of cognitive function has come under criticism by some for its test-retest reliability and practice effect whereby one naturally improves over time with repeated test taking. Polman C H et al., *Neurology* 74 Suppl 3: S8-15 (2010). In some embodiments, assessment of MacDonald dissemination in space and time finds use in the present methods. For example, for dissemination in space, lesion imaging, such as, by way of illustration, Barkhof-Tintore MR imaging criteria, may be used. For instance, the following criteria can be evaluated: (1) at least one gadolinium-enhancing lesion or 9 T2 hyperintense lesions; (2) at least one infratentorial lesion; (3) at least one juxtacortical lesion; (4) at least 3 periventricular lesions; and (5) a spinal cord lesion. Such imaging criteria can optionally be used in combination with evaluation for immunoglobulin abnormalities in the cerebrospinal fluid (CSF), for example. For dissemination in time, MR imaging can also be used. For example, if an MR imaging scan of the brain performed at ≥3 months after an initial clinical event demonstrates a new gadolinium-enhancing lesion, this may indicate a new CNS inflammatory event, because the duration of gadolinium enhancement in MS is usually less than 6 weeks. If there are no gadolinium-enhancing lesions but a new T2 lesion (presuming an MR imaging at the time of the initial event), a repeat MR imaging scan after another 3 months may be needed with demonstration of a new T2 lesion or gadolinium-enhancing lesion. In various embodiments, any one or more of these structural (anatomical) and functional tests may be used in conjunction with the present invention (e.g., to assess the effectiveness of a disclosed treatment method).

In some embodiments, patients having MS may be identified by criteria by the workshop on the diagnosis of MS (Poser et al., Ann. Neurol. 13:227, 1983). Briefly, under these criteria, an individual with clinically definite MS has experienced two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. (McDonald et al., 2001, Recommended diagnostic criteria for Multiple sclerosis: guidelines from the International Panel on the Diagnosis of Multiple Sclerosis, Ann Neurol 50:121-127). The McDonald criteria include the use of MRI evidence of CNS impairment over time to be used in diagnosis of MS, in the absence of multiple clinical attacks.

In some embodiments, treatment can be deemed to be effective if there is a statistically significant difference in the rate or proportion of exacerbation-free or relapse-free patients between a treated group and a placebo (or control) group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, or 20 months is particularly noteworthy. Clinical measurements include the relapse rate in one and two-year intervals, and a change in EDSS, including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images as described herein and known in the art.

In various embodiments, the gray matter loss or gray matter atrophy or gray matter volume, or any assessment or evaluation steps may be measured using an imaging technique and/or surrogate marker. Assessment of gray matter volume, and atrophy, can also be accomplished using MRI. Preferably, the MRI is able to distinguish between gray matter and white matter of the brain. For example, SIENAX software can be used to segment the MR images into gray matter/white matter/CSF compartments. Alternatively or in addition, FMRIB's Integrated Registration and Segmentation Tool (FIRST) can be used to segment the caudate, putamen, and thalamus, and BrainSuite13 can be used to segment the cerebral cortex. In certain embodiments, the MRI is able to distinguish between gray matter and white matter of the spinal cord. In various embodiments, the imaging technique is one or more of magnetic resonance imaging (MRI), 3T, axial T2, fast fluid-attenuated inversion recovery (FLAIR), double inversion recovery (DIR), phase-sensitive inversion recovery (PSIR), ultra high-field MRI, magnetization transfer imaging (MTI), T1-relaxometry, diffusion tensor imaging (DTI, including for example mean diffusivity (MD), fractional anisotropy (FA), radial diffusivity (Dr) and axial diffusivity (Da)), proton magnetic resonance spectroscopy (MRS)) and related techniques. In various embodiments, any of the techniques described in *Brain* (2002) 125 (8): 1676-1695, the contents of which are hereby incorporated by reference in their entirety, can be used alone or in combination to, for example, measure brain volume, gray matter atrophy. For example, the following may be used: linear regional measures; threshold-based measures; segmentation-based methods (e.g., CSF volume, BPF, WBR, BICCR, Fuzzy connectedness segmentation, SPM-based segmentation); template driven segmentation of the brain; SIENAX); registration-based methods (e.g., MIDAS (Medical Image Display and Analysis Software) method, voxel-based morphometry and brain surface modelling). Further, the present methods may employ any of the imaging methods described in *Am J Neuroradiol*. (2011) 32(2): 408-12, the contents of which are hereby incorporated by reference in their entirety.

In various embodiments, the surrogate marker is one or more of those described in *PLoS One* 8(9): e6617 (September 2013) or U.S. Pat. No. 8,772,225, the contents of which are hereby incorporated by reference in their entirety. For example, in some embodiments, the surrogate marker may be one or more of nogo receptor, kallikrein-6 (neurosin), cerebellin-1, ceruloplasmin, dickkopf-3 (rig-like 7-1), amyloid beta precursor-like protein 1, activated leukocyte cell adhesion molecule (CD 166), neural cell adhesion molecule 2, neural epidermal growth factor like 2/cerebral protein-12, clusterin (apolipoprotein j, complement lysis inhibitor), brevican, neuronal cadherin, chitinase-3-like 1 protein, neogenin, multifunctional protein MFP (collagen alpha 1 (XVIII) chain, endostatin), dystroglycan 1, contactin 2, ephrin type a receptor 4, neural cell adhesion molecule L1 like protein, and contactin 1.

In various embodiments, such measurements may be taken on a biological sample (e.g., cerebrospinal fluid (CSF), blood, a biopsy (e.g., frozen tissue specimen, cultured cells, formalin-fixed paraffin-embedded tissue specimen, etc.)). In some embodiments, the surrogate biomarker may be evaluated using one or more of mass spectrometry, immunohistochemical staining, western blotting, in cell western, immunofluorescent staining, ELISA, a radioimmunological assay (RIA), immunoblotting, a LINE blot, and fluorescent activating cell sorting (FACS). In some embodiments, the surrogate biomarker may also be evaluated on a nucleic acid level (e.g., low-to-mid-plex techniques, including but not limited to reporter gene assays, Northern blot, fluorescent in situ hybridization (FISH), and reverse transcription PCR (RT-PCR)) and higher-plex techniques, including but not limited to, serial analysis of gene expression (SAGE), DNA microarrays, Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP).

In some aspects, the present invention relates to a method of treating neurodegenerative disease (e.g., one or more forms of MS), in a patient having a decrease of white matter fA (fractional anisotropy) of about 10% (or about 5%, or about 6%, or about 7%, or about 8%, or about 9%, or about 10%, or about 11%, or about 12%, or about 13%, or about 14%, or about 15%), comprising administering to the patient an effective amount of an estrogen, which is optionally estriol and, optionally any one of the other therapies disclosed herein (e.g., one or more progestogens (e.g., progesterone)) at any of the doses and regimens described herein. In some aspects, the present invention relates to a method of preventing or reversing white matter fA loss in a patient in need thereof, comprising administering to the patient an effective amount of an estrogen, and, optionally any one of the other therapies disclosed herein (e.g., one or more progestogens (such as progesterone)) at any of the doses and regimens described herein. In some embodiments, white matter fA is measured using any of the methods described herein (e.g., imaging techniques and/or surrogate biomarkers), including, by way of example, diffusion tensor imaging (DTI). In various embodiments, white matter may be measured in various substructures including, for example, the optic nerve and cervical spinal cord. In various embodiments, the decrease of white matter fA, or prevention or reversal of white matter fA loss, is in one or more white matter substructures including, for example, the optic nerve and cervical spinal cord.

As described in the Examples below, a randomized, double-blind, placebo-controlled clinical trial was designed to ascertain whether treatment with an estrogen pill (estriol), used in combination with an FDA-approved standard treatment for MS (Copaxone®) for two years, can reduce brain gray matter atrophy as compared to treatment with a placebo pill in combination with the same major FDA-approved standard treatment for MS. Results from this study are presented in Example 1 below. Briefly, results from this study showed a reduction in total GM atrophy by adding estriol treatment as compared to placebo treatment to standard therapy.

Data in Example 1 are from the completed trial, as above, with Copaxone®) (glatiramer acetate) injections (20 mg/day) started at month 0.

Also as described in the Examples below, an ongoing randomized, double-blind, placebo-controlled clinical trial was designed to ascertain whether, in women, treatment with an estrogen pill (estriol), used in combination with major FDA-approved standard treatments for MS (Betaseron®, Extavia®, Rebif®, Avonex®, Copaxone®, Gilenya®, Aubagio®, or Tecfidera®) for one year, can improve cognitive testing as compared to treatment with a placebo pill in combination with the same major FDA-approved standard treatments for MS. Interim results from this ongoing study are presented in Example 2 below.

With respect to the estriol intervention, the study design includes continuous treatment with estriol, part of the time with norethindrone, and part of the time without norethindrone. That is, again with respect to the estriol intervention, the study can be understood as a series of consecutive periods, wherein for each period the subject continuously receives estriol and, for only a portion of each period, the subject also receives norethindrone.

In the experimental group, subjects receive standard MS treatment plus estriol 8 mg by mouth daily (continuously) plus norethindrone 0.7 mg by mouth daily for two weeks starting at month 6 and at months 9 and 12.

In the control group, subjects receive standard MS treatment plus estriol placebo by mouth daily (continuously) plus norethindrone placebo by mouth daily for two weeks starting at month 6 and at months 9 and 12.

Study subjects are 18- to 50-year-old women with diagnosis of clinically definite or MacDonald criteria relapsing-remitting MS, secondary-progressive MS, or primary-progressive MS; on a stable dose of Copaxone®, Betaseron®, Extavia®, Rebif®, Avonex®, Gilenya®, Aubagio®, or Tecfidera® for a minimum of 3 months duration prior to enrollment; and with no relapse within 30 days before trial enrollment. Excluded from the study are women on oral contraceptives (OCP), hormone replacement therapy (HRT), progesterone intrauterine devices (IUDs), or other sex hormones.

In the ongoing study, the primary outcome measure is change from baseline in cognitive function (processing speed), assessed by Paced Serial Addition Test (PASAT). Numerical test scores (ranging from 0-60) are acquired, then percent change for each subject at trial conclusion as compared to baseline is determined. A primary goal is to determine whether greater improvement as expressed as percent change occurs in the estriol group as compared to the placebo group.

Secondary outcome measures in the ongoing study include change from baseline in cognitive function as assessed by cognitive evoked potentials, measured in milliseconds; change from baseline in standard MS outcome measures (relapses, expanded disability status score (EDSS), 25-foot walk test, 9-hole peg test, low contrast visual acuity, MS Quality of Life, Modified Fatigue Impact Scale, and Beck Depression Inventory); change from baseline in cognitive function as assessed by a brief battery of cognitive tests; and safety.

Cognitive evoked potentials are recorded in msecs for each subject at baseline and conclusion. The percent improvement at conclusion as compared to baseline for each subject is determined. Group comparisons will reveal whether the percent improvement is greater in the estriol treated group as compared to the placebo treated group.

A brief battery of cognitive tests is administered, including: Processing speed: symbol digit modalities test (SDMT); Visual memory: 7/24 Spatial Recall Test, Benton Forms F & G; Verbal memory: Buschke Selective Reminding Test, Verbal Paired Associates; and Language: Word List Generation. Each subject is tested at baseline, month 6, and conclusion. Percent change at conclusion as compared to baseline is determined in each subject. Group comparisons will reveal which cognitive test within the battery had greater improvement in the estriol treated group as compared to the placebo treated group.

Safety is measured based on neurologic exams, laboratory tests (chemistries, complete blood count (CBC)), and breast and gynecologic exams. Having now described the present invention in detail, the same will be more clearly understood by reference to the following examples, which are included herewith for purposes of illustration only and are not intended to limit the invention.

EXAMPLES

Example 1—Use of Copaxone® and Estriol for the Treatment of Multiple Sclerosis

Sixteen sites randomized subjects 1:1 to oral estriol (8 mg daily) or oral placebo for 24 months (FIG. 1). A four week taper commenced at month 24 for both estriol and placebo. To avoid taking unopposed estrogens, the Estriol+GA subjects also received a progestin (0.7 mg norethindrone) daily for two weeks duration every three months starting at month 6, and Placebo+GA received a second placebo for progestin. All started GA injections (20 mg/day per day) within 2 months of randomization. Randomization had one stratification factor: GA treatment during screening. Each study site had separate examining and treating neurologists unaware of assignment. The examining neurologists performed neurologic assessments including EDSS, while treating neurologists managed patient care including treatment of relapses. 158 subjects were enrolled.

Each subject had a brain MRI done at month 0, 3, 6, 12, 24. The effect of estriol treatment as compared to placebo treatment on total (whole) brain gray matter (GM) atrophy was assessed since gray matter atrophy is a surrogate marker for permanent disability in MS. SIENAX software was used to segment the MR images into gray matter/white matter/CSF compartments from 10 estriol+Copaxone® (E+C) and 10 placebo+Copaxone® (P+C) subjects who had completed all 24 months of treatment. The GM volume change from the month 0 scan to the month 12 scan and then the volume change from the month 0 scan to the month 24 scan was calculated.

The GM volume change after 12 months was −9.5±3.8 mL (or −1.22±0.49%) in placebo+Copaxone® patients, and −1.0±2.0 mL (or −0.13±0.26%) in estriol+Copaxone® patients (p=0.071).

The GM volume change after 24 months was −12.5±5.0 mL (or −1.61±0.65%) in placebo+Copaxone® patients, and −2.0±4.4 mL (or −0.27±0.58%) in estriol+Copaxone® patients (p=0.138).

Thus the overall rate of GM atrophy in the placebo plus Copaxone® treated group was over 1.0% per year, while in the estriol plus Copaxone® treated group over the same period there was no significant atrophy. This represented a reduction in GM atrophy by adding on estriol treatment as compared to placebo treatment to standard therapy.

Figure 2:
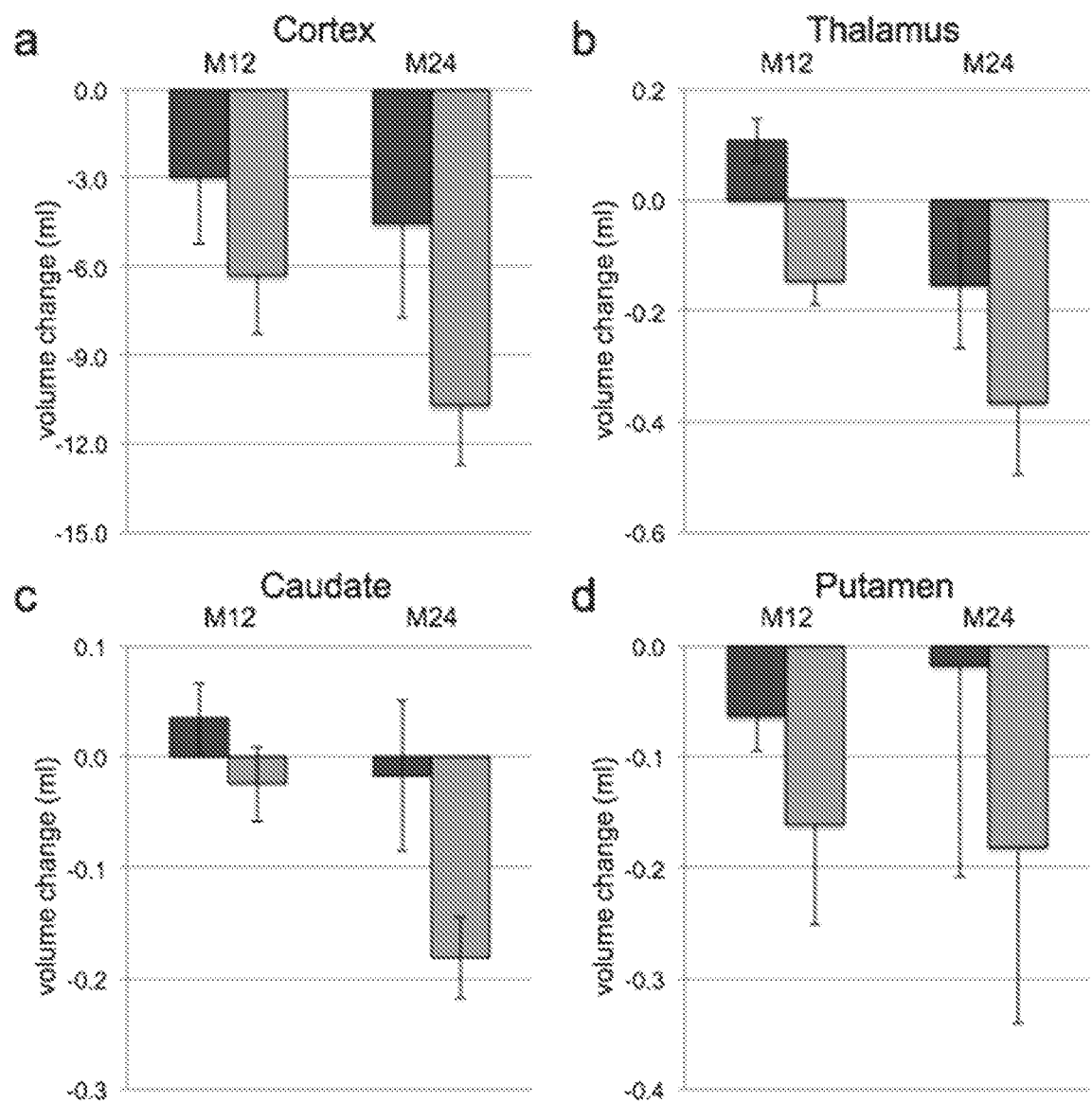
FIG. 2 includes four panels, identified as panels (A), (B), (C), and (D). Each panel corresponds to a bar graph depicting gray matter volume change in the cerebral cortex (A), thalamus (B), caudate (C), and putamen (D) in five patients treated with estriol plus Copaxone® (black bars) and five patients treated with placebo plus Copaxone® (gray bars). M12, comparison between month 0 (pre-treatment baseline) and month 12. M24, comparison between month 0 and month 24. Error bars, 1 SD.

The effects of estriol treatment on various brain GM regions were then assessed. FMRIB's Integrated Registration and Segmentation Tool (FIRST) was applied to segment the caudate, putamen, and thalamus, and BrainSuite13 to segment the cerebral cortex, from five subjects in the E+C group and five subjects from the P+C group. The volume change in each structure from the month 0 scan to the month 12 scan and then the volume change from the month 0 scan to the month 24 scan was calculated and plotted (FIG. 2). E+C patients demonstrated a trend towards less atrophy than P+C patients at both time points in all four structures. This data on less GM substructure volume loss with estriol treatment is consistent with the observation (above) of less whole GM volume loss with estriol treatment.

Example 2—Use of Copaxone® and Estriol for the Treatment of Multiple Sclerosis This example describes a randomized, double-blind, placebo-controlled human clinical trial for the treatment of multiple sclerosis using Copaxone® and estriol.

Enrollment Criteria

Eligible patients were females, an age of 18-50 years, a diagnosis of relapsing remitting multiple sclerosis as defined according to the McDonald criteria (Polman C. et al., Neurology 64:987 (200)), a baseline score of 0 to 4.5 on the Expanded Disability Status Scale (EDSS, which ranges from 0 to 10, with higher scores indicating more severe disability), and disease activity as evidenced by at least two documented relapses in the previous 24 months before screening or as evidenced by at least one documented relapse within 24 months before screening with a history of at least one gadolinium-enhancing lesion on a brain or cord magnetic resonance imaging (MRI) scan performed at least 3 months before or 3 months after the clinical relapse. Key exclusion criteria were progressive forms of multiple sclerosis, other clinically significant diseases, pre-specified laboratory test abnormalities, possible malignancy on mammogram or uterine ultrasound, exposure to glatiramer acetate for longer than 2 months before randomization, relapse or steroid use within 30 days prior to randomization, use of any interferon, ACTH, corticosteroids, intravenous immunoglobulins, or other listed MS treatments within 2 months before screening, those who were pregnant, breastfeeding, or trying to get pregnant, those not willing to discontinue other hormonal treatments, those who underwent surgical or natural menopause for longer than 1 or 3 years, respectively, with no hormone replacement therapy, those who had ever been treated with a major immunosuppressive contraindicated treatment.

TABLE 1

Baseline Characteristics of the Intention-to-Treat Population.*

| Patient Characteristics | Estriol + GA (N = 82) | Placebo + GA (N = 76) |
|---|---|---|
| Age - yr | 37.7 ± 7.6 | 37.1 ± 7.3 |
| Race - no. (%)† | | |
| Caucasian | 65 (79.3) | 62 (81.6) |
| Black | 9 (11.0) | 7 (9.2) |
| Hispanic | 7 (8.5) | 6 (7.9) |
| Other | 1 (1.2) | 1 (1.2) |
| Time since diagnosis - yr | 3.3 ± 4.6 | 2.9 ± 4.5 |
| Number of previous relapses | | |
| Within 1 yr before screening | 1.5 ± 0.7 | 1.5 ± 0.7 |
| Within 2 yr before screening | 2.0 ± 0.7 | 2.3 ± 0.9 |
| Prior GA treatment | | |
| Never | 25 (30.5) | 27 (35.5) |
| Previously | 17 (20.7) | 6 (7.9) |
| During screening | 40 (48.8) | 43 (56.6) |
| Prior treatment with any interferon - no. (%)‡ | | |
| No | 59 (72.0) | 50 (65.8) |
| Yes | 23 (28.0) | 26 (34.2) |
| Mean score on EDSS¶ | 2.2 ± 1.2 | 2.1 ± 1.1 |
| EDSS sore at baseline - no. (%)¶ | | |
| 0 | 9 (11.0) | 6 (7.9) |
| 1.0 or 1.5 | 16 (19.5) | 21 (27.6) |
| 2.0 or 2.5 | 27 (32.9) | 24 (31.6) |
| 3.0 or 3.5 | 25 (30.5) | 22 (29.0) |
| 4.0 | 4 (4.9) | 2 (2.6) |
| 5.5 | 1 (1.2) | 1 (1.3) |
| Gadolinium-enhancing lesions number | 1.0 ± 2.3 | 0.9 ± 2.0 |
| Active lesions on brain MRI - no. (%) | | |
| No | 55 (67.9) | 53 (70.7) |
| Yes | 26 (32.1) | 22 (29.3) |
| Volume of lesions on T2 weighted Images - cm³ | 6.8 ± 8.9 | 7.7 ± 11.2 |

*Plus-minus values are means +/− SD. All patients were included as the intention-to-treat population who underwent randomization, except those with no data after randomization. There were no significant differences between baseline clinical or demographic characteristics between the study groups.
†Race was self-reported.
‡Patients may have received more than one prior multiple sclerosis medication. Patients may have received other non-approved therapies for multiple sclerosis before enrollment in the study. The percentage of patients receiving medication for multiple sclerosis before study entry was balanced across treatment groups.
¶Scores on the Expanded Disability Status Scale (EDSS) ranged from 0 to 10, with higher scores indicating a greater degree of disability. The baseline EDSS score was higher than inclusion criteria of 4.5 in two patients (EDSS = 5.5), one in each study group that were 4.5 at first screening visit, but 5.5 at baseline. One patient in the Estriol + GA group did not have a confirmed relapse within 24 months prior to randomization, with enrollment based on disease activity evidenced by MRI enhancing lesions.

Efficacy Measures

Standardized neurologic assessments, including an EDSS assessment, were performed at months 0, 3, 6, 12, 18 and 24, and at the time of a suspected relapse (as an additional unscheduled visit). EDSS assessments were performed by physicians who were trained either by in-person training or online (www.Neurostatus.net). MRI scans were obtained at screening and at months 0, 3, 6, 12 and 24. Subjects were seen or contacted every 3 months for compliance assessments and for dispensing medications.

The primary efficacy end point was the annualized relapse rate. A relapse was defined as the appearance of new neurological symptoms or the worsening of pre-existing symptoms, lasting at least 48 hours in a subject who had been neurologically stable or improving in the previous 30 days, accompanied by an objective change in a neurological examination (i.e., a worsening of 0.5 or more points on the EDSS or a worsening by 1.0 or more points on the pyramidal, cerebellar, brainstem or visual functional system scores, not due to fatigue alone and not associated with fever or infection). The treating physician made the decision concerning whether the relapse criteria had been met, incorporating whether a change in EDSS had been documented by the examining physician. Both treating and examining physicians were unaware of study group assignments. The standard treatment for relapse was a 3-5 day course of glucocorticoids at the discretion of the treating neurologist.

Secondary efficacy end points included the proportion of subjects with a relapse over all 24 months, a change in PASAT cognitive testing, a sustained improvement in PASAT cognitive testing (as defined by an increase of at least 3 points sustained over at least 6 months), a change in EDSS scores from baseline, disability progression (as defined by an increase in EDSS of at least 1.0 point in subjects with a baseline score of 1.0 or higher, or by an increase of at least a 1.5 points in subjects with a baseline score of 0, each sustained for at least 6 months). Tertiary end points included gray matter atrophy on MRI.

Study Conduct and Monitoring Schedule

Patients were randomized to Copaxone® (glatiramer acetate) injections (20 mg/day) and oral estriol (8 mg/day) or to Copaxone® injections and placebo for a 24-month treatment duration. Gynecologists examined the patients before, during, and after the study. Each patient was examined at three- to six-month intervals during the trial. Patients also underwent mammograms before and after the study. In addition, at baseline, three months, six months, 12 months, 18 months, and 24 months, the investigators measured participants' estriol levels, and assessed for MS relapses and MS-related disabilities.

A total of 82 patients received Copaxone® plus estriol, and 76 patients received Copaxone® plus placebo. Baseline characteristics were similar in both patient groups. Participants' mean age at entry was approximately 38, and their mean EDSS score at entry was 2.2. Estriol levels in serum were in a mid-pregnancy range in the estriol-treated group. To ensure breast and uterus safety, every three months the patients took norethindrone 0.7 mg once a day for 14 days. This hormone regimen was found to be safe and well tolerated with regard to serious adverse events, adverse events, general exams, blood chemistries, and hematological studies, as well as for gynecological outcomes (see Table 2). Irregular menses occurred more with Estriol+GA (P<0.001), while vaginal infections occurred more with Placebo+GA (P<0.05), with no increase in discontinuations due to either.

TABLE 2

Adverse Events and Serious Adverse Events

| Adverse Events† | Estriol + GA (N = 82) | Placebo + GA (N = 76) |
| --- | --- | --- |
| Any adverse event - no. of events, [no of pts, % of pts] | 480 [76, 93%] | 392 [67, 87%] |
| Most frequent events - no. of events [no of pts, % of pts] | | |
| Copaxone injection area abnormalities | 51 [26, 32%]* | 30 [14, 18%] |
| Upper respiratory infection | 33 [22, 27%] | 38 [26, 34%] |
| Irregular menses/spotting | 26 [19, 23%]*** | 4 [3, 4%] |
| Urinary tract infection | 23 [15, 18%] | 16 [10, 13%] |
| Fatigue | 15 [13, 16%] | 10 [8, 10%] |
| Depression/anxiety | 14 [12, 15%] | 10 [9, 12%] |
| Menstrual flow amount increased | 12 [11, 13%] | 8 [6, 8%] |
| Headache | 11 [9, 11%] | 12 [11, 14%] |
| Nausea/vomiting | 9 [7, 9%] | 5 [5, 6%] |
| Sinusitis | 6 [6, 7%] | 14 [10, 13%]* |
| Arm/leg numbness, tingling | 7 [6, 7%] | 10 [7, 9%] |
| Gastroenteritis | 7 [5, 6%] | 4 [3, 4%] |
| Dizziness | 5 [4, 5%] | 10 [7, 9%] |
| Vision problem (blurry, double) | 6 [4, 5%] | 7 [7, 9%] |
| Back pain | 5 [4, 5%] | 5 [5, 6%] |
| Menstrual cramp | 4 [4, 5%] | 5 [4, 5%] |
| Insomnia | 4 [4, 5%] | 4 [4, 5%] |
| Heart palpitation | 2 [2, 2%] | 4 [4, 5%] |
| Shingles | 7 [2, 2%] | 4 [4, 5%] |
| Vaginal infection | 1 [1, 1%] | 9 [8, 10%]** |
| Adverse events leading to discontinuation - no. (%) | 5 (6%) | 5 (6%) |
| Severe adverse events‡ | 9 [8, 10%] | 12 [10, 13%] |
| MS relapse | 2 [2, 2%]¶ | 6 [5, 6%]¶ |
| Pregnancy termination | 2 [2, 2%] | 0 |
| UTI | 1 [1, 1%] | 1 [1, 1%] |
| Migraine headache related eye pain | 1 [1, 1%] | 0 |
| Heart failure | 1 [1, 1%] | 0 |
| Pace maker implantation | 1 [1, 1%] | 0 |
| Pyelonephritis | 1 [1, 1%] | 0 |
| Systolic heart failure | 1 [1, 1%] | 0 |
| Accidently took other's drug | 0 | 1 [1, 1%] |
| Acute appendicitis | 0 | 1 [1, 1%] |
| B-cell lymphoma§ | 0 | 1 [1, 1%] |
| Car accident related body numbness | 0 | 1 [1, 1%] |
| Right knee replacement | 0 | 1 [1, 1%] |
| Other safety events monitored | | |
| Uterus | | |
| Endometrial thickness >8 mm (ultrasound) - no. (%) | 24 (29) | 27 (36) |
| Endometrial biopsies performed§§ - no. (%) | 9 (11) | 6 (8) |

TABLE 2-continued

Adverse Events and Serious Adverse Events

| Adverse Events† | Estriol + GA (N = 82) | Placebo + GA (N = 76) |
|---|---|---|
| Fibroids (ultrasound) - no. (%) | 8 (10) | 8 (11) |
| Abnormal proliferation on biopsy - no. (%) | 0 | 0 |
| Breast | | |
| Fibrocystic disease on clinical exam | 5 (6) | 4 (5) |
| Mammogram with malignancy | 0 | 0 |

†All patients who took at least one dose of study drug were included. However, among the 6 patients who dropped shortly after baseline visit, five did not have safety evaluation data and were excluded from the safety analysis. The listed events reported by % were rounded up to nearest integer. The events are listed by decreasing incidence in the Estriol + GA group, within each category.
*AE significantly higher in one treatment group compared to the other;
***indicating P <0.001,
**indicating P < 0.05, and
*indicating P < 0.10.
‡SAE patients were all hospitalized, but none had severe or immediately life-threatening condition.
§This patient, in the placebo group, discontinued the study at the time of B-cell lymphoma diagnosis when was on study for 12 months and died 17 months later.
¶In Estriol + GA group, both patients discontinued the study: 1 before and 1 after Month 12. In Placebo + GA group, 3 patients discontinued the study: 1 before and 2 after Month 12.
§§Four patients had multiple uterine endometrial biopsies: two patients had two biopsies each in the Estriol + GA group and two patients had three biopsies each in the Placebo + GA group. No abnormal proliferation was found.
Note:
No laboratory abnormalities occurred significantly more frequently in either treatment group.

Safety assessments, including clinical, blood laboratory safety testing and assessments of estriol levels, occurred at months 0, 3, 6, 12, 18, and 24. On study blood tests included complete blood count (CBC) with differential and platelets; chemistry panel including sodium, potassium, creatinine, BUN, glucose, total protein, albumin, bilirubin (total), alkaline phosphatase, AST (SGOT), and ALT (SGPT), and lipid profile (HDL, LDL and triglycerides, cholesterol. Gynecologic exams were done at month 0, 6, 18 and at month 24 exit, with uterine ultrasounds at months 6, 18 and at month 24 exit. Mammograms were done in screening and at month 24 exit. Adverse event analysis was based on the percentage of patients who discontinued the study and the percentage of patients who discontinued the study possibly due to adverse events.

Statistical Analysis

The sample size was determined based on the primary end point of annualized relapse rate. A total sample of 150 eligible patients would provide approximately 80% power at a two-sided significance level of 0.10 for this phase II clinical trial to detect the difference in the annualized relapse rate of 0.76 vs 1.18 for Estriol plus GA group and the Placebo plus GA group in 2 years.

Intention-to-treat analyses were carried out for all end points. For the primary endpoint, a negative binomial regression model was used to compare both 12 months and 24 months annualized relapse rates between Estriol+GA versus Placebo+GA groups adjusted for covariates. To control the overall type I error, a sequential testing procedure was applied. A hierarchical statistical approach was used whereby results in the first 12 months of treatment would be assessed, and, if and only if, significance were met, results in the entire 24 months of treatment would be assessed. The earlier timepoint was compared first since GA requires time to reach full efficacy, potentially providing a greater window to detect efficacy 12 months after initiation of GA and study drug treatment. Consistent with a phase 2 study using a clinical outcome, a p-value<0.10 was considered statistically significant.

For the time to first relapse analysis, Kaplan Meier curves and log-rank test were used to estimate and compare the relapse free probabilities of the two treatment groups. Cox proportional hazards model was used to compare the time to relapse free probabilities between two groups adjusting for covariates. The fixed effects include treatment groups (Estriol+GA vs Placebo+GA), baseline lesion number, age and baseline EDSS score. The random effect of subject is included in the model to account for within subject correlation.

Linear mixed effects model was carried out to compare the percent change in whole gray matter and cortical gray matter between treatment groups. For the exploratory endpoints of EDSS, PASAT, and brain volume measures, linear mixed effects model was used to compare treatment groups at 12 and 24 months. Linear mixed effects model was carried out to evaluate the association between PASAT change and percent brain volume change.

Multiple imputation on the missing data was also performed according to the pattern mixture model as a sensitivity analysis. The pattern mixture model provides the analysis with the possibility of non-random dropout. The missing data were sequentially imputed by the follow up time and the imputation model assumed that the treatment effect for patients after drop out is the same as taking placebo.

Patients

A total of 164 patients were randomized, of which 158 received study drug and had at least one visit thereafter (intention-to-treat population). Of the 158 patients, 82 were assigned to the Estriol+GA group and 76 to the Placebo+GA group (FIG. 1). Baseline demographics and disease characteristics were well balance across both patient groups (Table 1).

The rate of discontinuation was similar between groups (FIG. 1). A total of 60 patients (73.2%) in the Estriol plus GA group and 56 (73.7%) in the Placebo plus GA group completed the 24 month study treatment duration. Of the 158 patients, 15.8% discontinued the study during the first year (7.6% in the Estriol plus GA group and 8.2% in the Placebo plus GA group), and an additional 10.7% discontinued the study during the second year (6.3% and 4.4%, respectively). Reasons for discontinuation did not differ between groups. The most common reasons for discontinuation were lost to follow up or patient's decision based on family issues or time constraints.

Primary Outcome Measure

Figure 3:
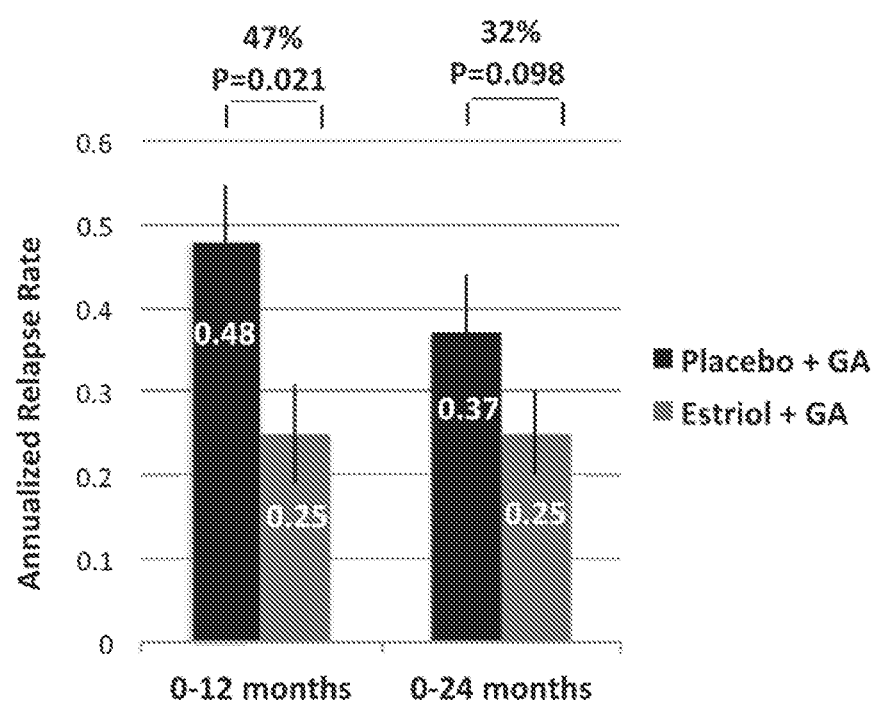
FIG. 3 is a bar graph depicting annualized relapse rates with Copaxone® plus estriol treatment as compared to Copaxone® plus estriol placebo treatment.

The primary outcome measure for disease efficacy was annualized relapse rate. While most Phase II trials used surrogates or biomarkers as the primary outcome, the trial focused on an outcome measure acceptable for approval by the FDA. Since this was a Phase II trial, it was powered to reduce relapses by one third more in the Copaxone® plus estriol group as compared to the Copaxone® plus placebo group, with a targeted p value of p=0.10 at the end of study which was 24 months. As shown in FIG. 3, after 24 months of treatment the primary outcome measure was attained by reducing relapse rates by 32% (p=0.11) in the Copaxone® plus estriol group as compared to the Copaxone® plus placebo group. Surprisingly, after only 12 months of treatment, the relapse rate was reduced by 47% (p=0.02) in the Copaxone® plus estriol group as compared to the Copaxone® plus placebo group, see FIG. 3. In the entire 24 months of treatment, the relapse rate was reduced by 32% (P=0.098) in the Estriol plus GA group as compared to the Placebo plus GA group. Thus, in addition to finding that Copaxone® plus estriol treatment had significant benefit in reducing the frequency of relapses over 24 months, the combination treatment also had a more rapid onset of action as compared to Copaxone® plus placebo.

Regarding temporal patterns, relapse rates remained low and unchanged from month 12 (0.25) to month 24 (0.25) with Estriol+GA, while relapse rates decreased gradually from month 12 (0.48) to month 24 (0.37) with Placebo+GA. A more rapid onset of efficacy with Estriol+GA was also observed when examining the proportion of subjects relapse free over 24 months, with differences beginning at 6-12 months, favoring Estriol+GA, P=0.096.

These results were surprising given that estriol treatment was not compared to a true placebo, but rather was tested in combination with standard-of-care therapy (Copaxone®).

Since anti-inflammatory drugs the FDA has approved have so far required much larger sample sizes to show a significant reduction in relapse rates, even as compared to a true placebo, the results of the study adding estriol to Copaxone® suggest a novel mechanism of action, a mechanism never before observed in MS. We hypothesize, based on our surprising findings, that this novel mechanism of action may entail direct effects of estriol treatment on preserving gray matter (total as well as substructure) volumes.

TABLE 3

Clinical End Points*

| End Point | Estriol + GA (n = 82) | Placebo + GA (n = 76) |
|---|---|---|
| Annualized relapse rate in 12 months | | |
| Rate (95% CI)† | 0.25 (0.16-0.40) | 0.48 (0.33-0.69) |
| Adjusted rate ratio E + GA vs. P + GA (95% CI)§ | 0.51 (0.29-0.90)*[1] | |
| Annualized relapse rate in 24 months | | |
| Rate (95% CI)† | 0.25 (0.17-0.37) | 0.37 (0.25-0.53) |
| Adjusted rate ratio E + GA vs. P + GA (95% CI)§ | 0.65 (0.39-1.08)*[2] | |
| Time to first confirmed relapse | | |
| Proportion of pts with relapse at 12 months % (95% CI)‡ | 22.8 (15.0-33.7) | 33.1 (23.5-45.2) |
| Proportion of pts with relapse at 24 months % (95% CI)‡ | 33.3 (23.8-45.4) | 42.9 (32.1-55.5) |
| Adjusted hazard ratio E + GA vs. P + GA (95% CI)¶ | 0.63 (0.36-1.09)*[3] | |
| Time to disability progression | | |
| Proportion of pts with progression at 24 months % (95% CI)‡ | 11.4 (5.9-21.7) | 15.8 (8.8-27.6) |
| Adjusted hazard ratio E + GA vs. P + GA (95% CI)¶ | 0.81 (0.32-2.07) | |
| EDSS score reduction from baseline to Month 24 | | |
| Mean ± SD, Median | 0.29 ± 0.98, 0.5 | 0.05 ± 1.13, 0.0 |

*Plus-minus values are means ± SD. CI denotes confidence interval, E + GA for Estriol + GA, and P + GA for Placebo + GA.
†Annualized relapse rates were calculated based on negative binomial regression.
§Relapse rate ratio was estimated using negative binomial regression with adjustment for age, baseline EDSS (<2 vs. ≥2), number of relapse 12 months prior study entry (0-1 vs. >1), MS duration (<1 vs. ≥1 year), prior GA treatment (never vs. past/current), and prior interferon treatment (yes vs. no).
‡Values were calculated using the Kaplan-Meier product-limit method. Progression defined as EDSS increase of at least 1.0 point in subjects with baseline score of 1.0 or higher or increase of at least 1.5 points with baseline score of 0, each sustained for at least 6 months.
¶Hazard ratio was estimated using Cox proportional hazard regression. For relapse, age, baseline EDSS (<2 vs ≥2), number of relapse 12 months prior study entry (0-1 vs. >1), MS duration (<1 vs. ≥1 year), prior GA treatment (never vs. past/current), and prior interferon treatment (yes vs. no) were adjusted; for EDSS progression, age and baseline EDSS (<2 vs. ≥2) were adjusted.
*[1] P = 0.021;
*[2] P = 0.098;
*[3] P = 0.096

Disability Assessment

Figure 6:
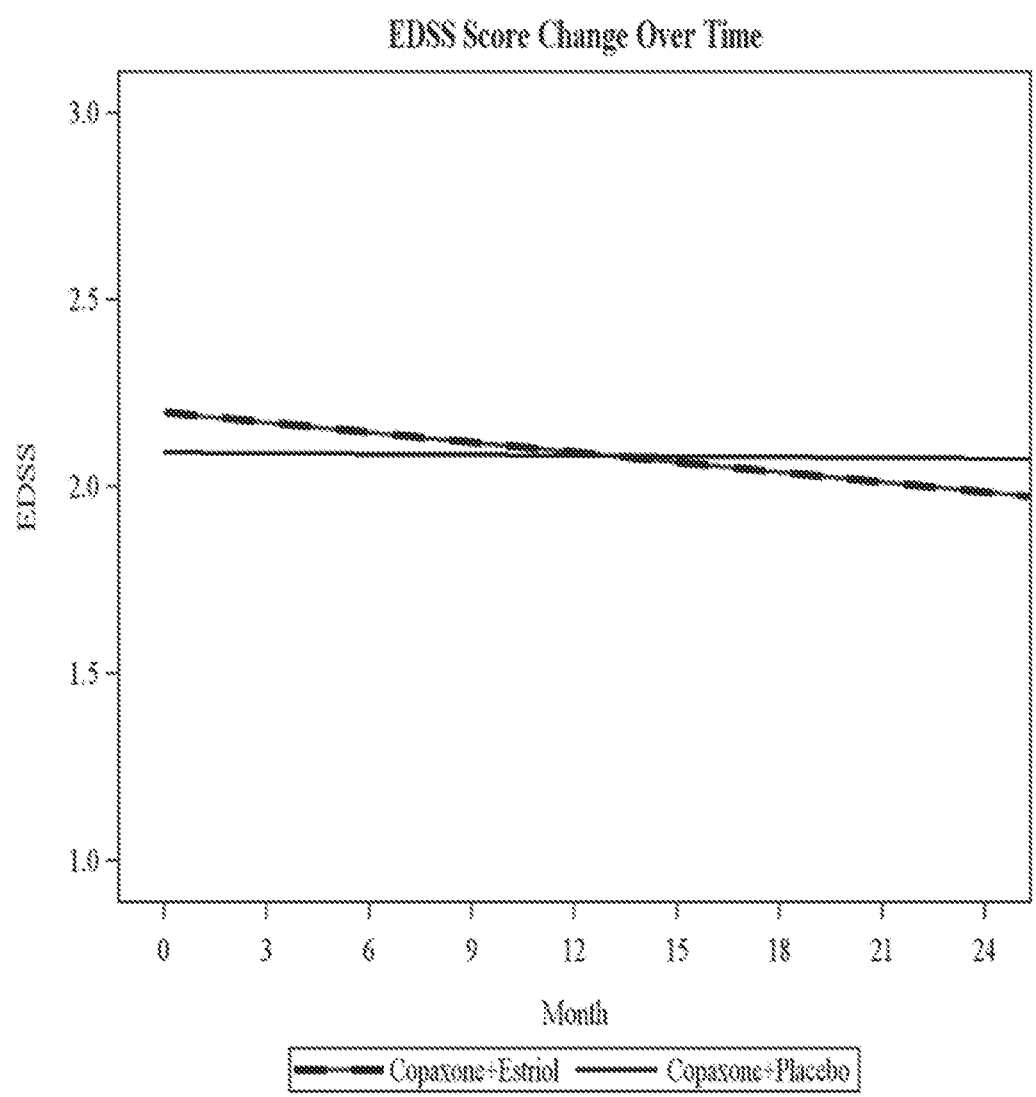
FIG. 6 is a graph depicting Expanded Disability Status Scale (EDSS) scores over 24 months for treatment groups receiving Copaxone® plus estriol (slope=−0.11, p=0.06) or Copaxone® plus estriol placebo (slope=−0.01, p=0.90).

Exploratory disability outcomes revealed promising trends for improvement in the Estriol plus GA group. The Expanded Disability Status Scale (EDSS) is a standard composite disability score used extensively in MS trials. Higher scores indicate worse disability. This composite covers a variety of disabilities (including ambulation, vision, cognition, coordination, etc.), but the scoring is not linear and the composite score is understood to be principally an indicator of the level of disability in ambulation. While there was no change in the EDSS scores for the Copaxone® plus placebo treatment group, the Copaxone® plus estriol treatment group showed a significant decrease (i.e., improvement) in this disability score (FIG. 6). The probability of disability worsening or EDSS progression (as defined by an increase in EDSS of 1 point for over 6 months) was 15.8% for the Placebo plus GA group, and 11.4% for the Estriol plus GA group (Table 3). EDSS scores were then assessed for possible improvement with combination treatment. While EDSS scores in the Placebo plus GA group were stable and unchanged over the entire 24 month treatment duration, the Estriol plus GA group showed a significant improvement in EDSS scores by the end of study, month 24, with a median change in EDSS of a half step (EDSS absolute median change=−0.5, p=0.03), however group differences in EDSS improvement were not powered for significance (FIG. 7A).

Another clinical disability measure with treatment effects was the timed 25-foot walk test. This test measures how many seconds it takes to walk 25 feet, with higher scores indicating worse disability. The walk time was significantly increased in the Copaxone® plus placebo group (p=0.03), while it was slightly decreased in the Copaxone® plus estriol group, together resulting in a significant between-group difference (p=0.02). Together these data show a gradual worsening in walking times in the Copaxone® plus placebo treated group, which did not occur in the Copaxone® plus estriol treated group. This beneficial effect of estriol treatment on 25-foot walking times is consistent with the beneficial effect of estriol treatment on EDSS scores since the latter is weighted toward being an indicator of ambulation.

Figure 4:
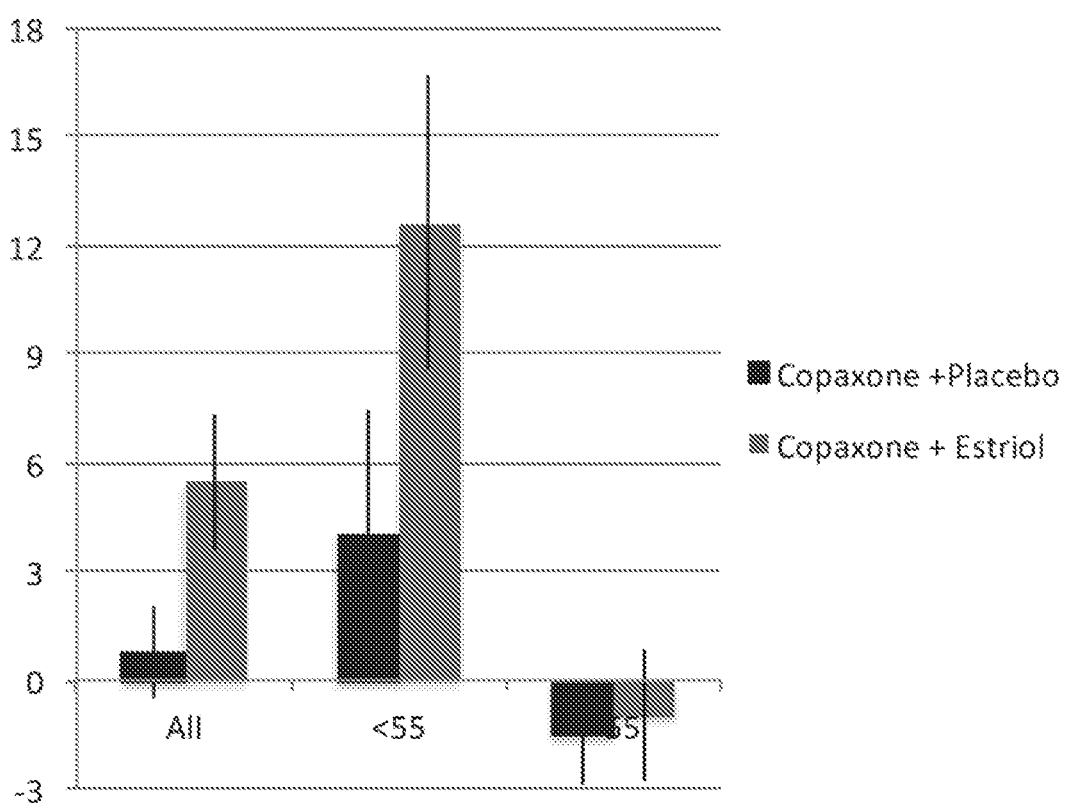
FIG. 4 is a bar graph depicting Paced Serial Addition Test (PASAT) cognitive test scores for all subjects (All), subjects with baseline scores of less than 55/60 (<55), and subjects with baseline scores greater than or equal to 55/60 (≥55). Comparison is made between treatment groups receiving Copaxone® plus estriol or Copaxone® plus estriol placebo. Data are expressed as percent change from baseline in each treatment group.

There were no significant differences between groups in the Multiple Sclerosis Functional Composite (MSFC), which reflects a composite of scores including the Paced Auditory Serial Addition Test (PASAT) for cognition, the 9 hole peg test and the 25 foot walk test (Table 4). However, an interesting effect of combination treatment was observed on cognitive disability. A perfect PASAT score is 60, with scores lower than 55 serving as a continuous variable for disability. By 12 months of treatment, PASAT scores improved significantly as compared with scores at baseline, by approximately 6% (i.e., 3 points) among patients receiving Estriol plus GA, while no significant improvement was observed in those receiving Placebo plus GA, (p=0.04 between group difference, all adjusted for covariates of age, education and baseline scores). Subgroup analysis showed that this improvement in PASAT scores in the Estriol plus GA group at month 12 was due to improvements in those with more cognitive disability at baseline (FIG. 4). After 12 months of treatment, patients receiving Copaxone® plus estriol continued to have high PASAT scores to the end of study at month 24, while participants receiving placebo began to show improved PASAT scores by month 24. Notably, a change of six or more points in tests of processing speed in MS is considered to be clinically significant. Further, Copaxone® plus estriol treatment improved function in those with significant cognitive disability, rather than merely slowing cognitive decline. This represents repair of disability, not merely prevention of worsening. This beneficial effect on PASAT scores at 12 months in the Estriol plus GA group could not be attributed to practice effects of repeated testing since the comparison was with the Placebo plus GA group tested at identical time points.

Figure 5:
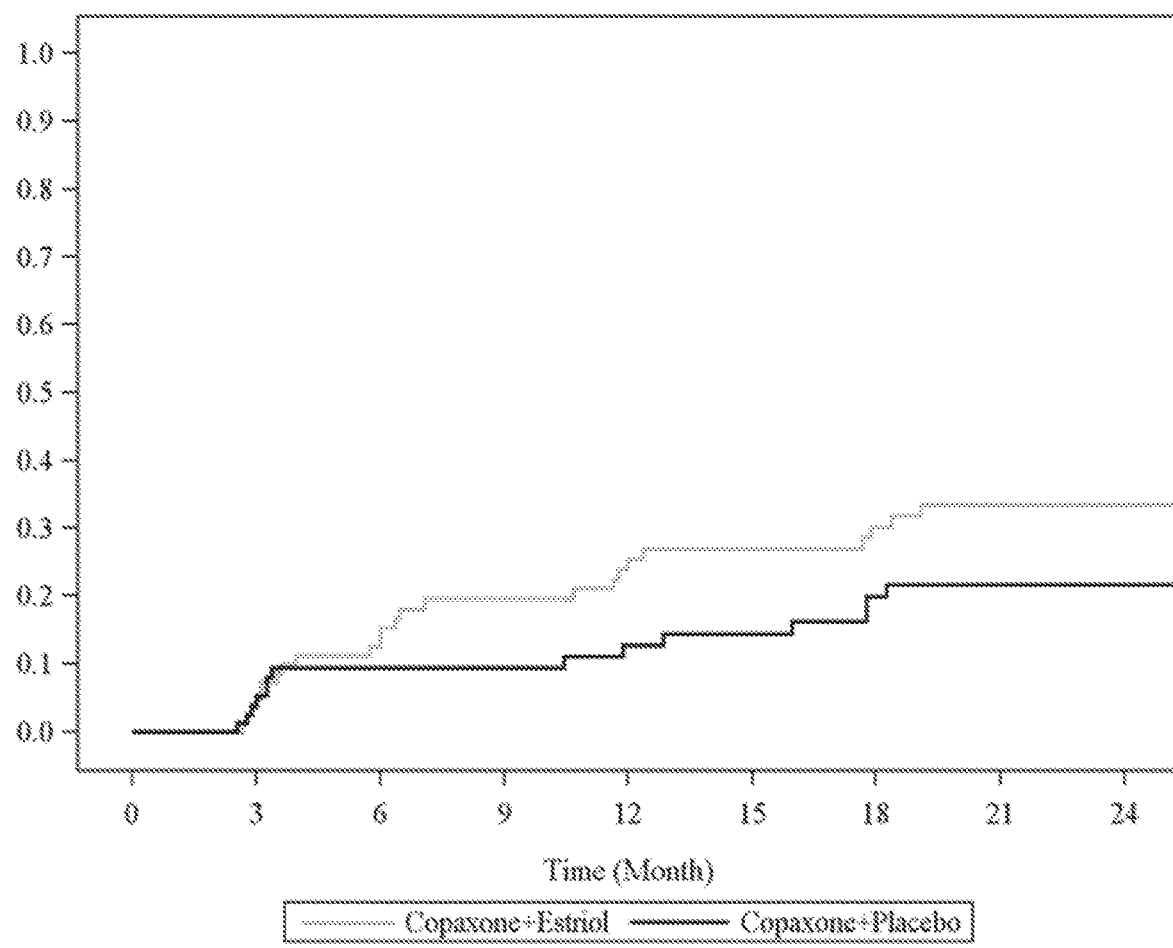
FIG. 5 is a graph depicting the proportion of all subjects who had sustained improvement of 3 points in PASAT scores for 6 months. Comparison is made between treatment groups receiving Copaxone® plus estriol (upper curve) or Copaxone® plus estriol placebo (lower curve).

Next it was shown that the improvement in PASAT cognitive test scores was sustained when subjects were followed for the entire 24 month period, p=0.02 (FIG. 5).

In addition, the beneficial effects of estriol treatment on cognitive function were shown using another cognitive test, the 7/24 spatial recall test (for spatial memory). While initial encoding of information did not differ between groups, the number of subjects with perfect scores for immediate recall (p=0.006) and delayed recall (p=0.04) was higher in the Copaxone® plus estriol treated group as compared to the Copaxone® plus placebo treated group over the entire 24 month treatment duration. Such rapid and potent effects on cognition that were observed in the Copaxone® plus estriol group as compared to the Copaxone® plus placebo group were surprising and point to a novel effect on cognitive disability not seen before with other FDA-approved MS drugs.

TABLE 4

| | | |
|---|---|---|
| | Multiple Sclerosis Functional Composite (MSFC) | |
| End Point | Estriol + GA (N = 82) | Placebo + GA (N = 76) |
| MSFC Score[a] | | |
| Baseline score (Mean ± SD, Median) | −0.04 ± 0.69, 0.05 | 0.06 ± 0.79, 0.24 |
| Change from baseline at Month 12 | N = 70 | N = 58 |
| Mean ± SD, Median | 0.13 ± 0.37 | 0.06 ± 0.38 |
| Change from baseline at Month 24 | N = 60 | N = 54 |
| Mean ± SD, Median | 0.10 ± 0.35 | 0.09 ± 0.43 |
| PASAT3 score - All Patients[a] | | |
| Baseline score (Mean ± SD, Median) | 51.0 ± 8.9, 55 | 52.3 ± 9.1, 56 |
| change from baseline at Month 12 | N = 70 | N = 61 |
| Mean ± SD, Median | 1.9 ± 5.6, 1.0** | 0.1 ± 4.5, 0 |
| change from baseline at Month 24 | N = 60 | N = 55 |
| Mean ± SD, Median | 1.1 ± 4.0, 1.0 | 1.1 ± 4.3, 0 |
| % change from baseline at Month 12 | N = 70 | N = 61 |
| Mean ± SD, Median (%) | 5.5 ± 15.6, 1.8** | 0.8 ± 9.9, 0 |
| % change from baseline at Month 24 | N = 60 | N = 55 |
| Mean ± SD, Median (%) | 2.9 ± 10.6, 1.7 | 2.7 ± 10.3, 0 |
| PASAT3 score - Patients with baseline score <55[a] | N = 39 | N = 33 |
| Baseline score (Mean ± SD, Median) | 43.7 ± 7.6, 45 | 44.7 ± 9.1, 49 |
| change from baseline at Month 12 | N = 33 | N = 25 |
| Mean ± SD, Median | 4.7 ± 6.6, 4.0* | 1.6 ± 6.0, 1.0 |

TABLE 4-continued

Multiple Sclerosis Functional Composite (MSFC)

| End Point | Estriol + GA (N = 82) | Placebo + GA (N = 76) |
|---|---|---|
| change from baseline at Month 24 | N = 26 | N = 23 |
| Mean ± SD, Median | 2.3 ± 5.2, 3.5 | 3.0 ± 5.9, 4.0 |
| % change from baseline at Month 12 | N = 33 | N = 25 |
| Mean ± SD, Median (%) | 12.6 ± 19.9, 7.6* | 4.0 ± 14.0, 3.8 |
| % change from baseline at Month 24 | N = 26 | N = 23 |
| Mean ± SD, Median (%) | 6.4 ± 14.8, 6.8 | 6.9 ± 14.7, 9.1 |
| 9-Hole Peg Test[b] | | |
| Baseline value (Mean ± SD, Median) | 19.7 ± 3.8, 19.0 | 19.1 ± 2.7, 18.8 |
| Change from baseline at Month 12 | N = 70 | N = 63 |
| Mean ± SD, Median | −0.6 ± 1.5, −0.6 | −0.1 ± 1.8, −0.4 |
| Change from baseline at Month 24 | N = 60 | N = 56 |
| Mean ± SD, Median | −0.1 ± 3.5, −0.6 | −0.4 ± 1.5, −0.5 |
| 25-foot Walk Time[b] | | |
| Baseline value (Mean ± SD, Median) | 4.9 ± 1.0, 4.7 | 4.9 ± 1.5, 4.5 |
| Change from baseline at Month 24 | N = 70 | N = 60 |
| Mean ± SD, Median | 0.1 ± 0.8, 0.1 | 0.0 ± 0.9, 0.0 |
| Change from baseline at Month 24 | N = 60 | N = 55 |
| Mean ± SD, Median | −0.1 ± 0.6, −0.0 | 0.1 ± 1.1, 0.1 |

[a]Change from baseline positive value indicate improvement for MSFC and PASAT3
[b]Change from baseline positive value indicate worsening for 9-Hole Peg test and 25-Foot Walk Time.
**P < 0.05, student t-test comparing the means of the two study groups
*P < 0.10, student t-test comparing the means of the two study groups
§ Values were calculated using the Kaplan-Meier product-limit method.

In contrast to month 12 observations, absolute PASAT scores were no different at month 24 in the Estriol plus GA group compared to the Placebo plus GA group (FIG. 7B; Table 4). This was due to both a trend for improvement in the Placebo plus GA group as well as a trend for worsening in the Estriol plus GA group. To address whether a trend for worsening in the Estriol plus GA group at month 24 might be related to the decrease in estriol levels at month 24, correlations between estriol levels and improvement in PASAT scores were assessed. Indeed, higher estriol levels correlated with greater improvement in PASAT scores (p=0.03 for all patients; p=0.07 for Estriol+GA patients only).

Figure 7:
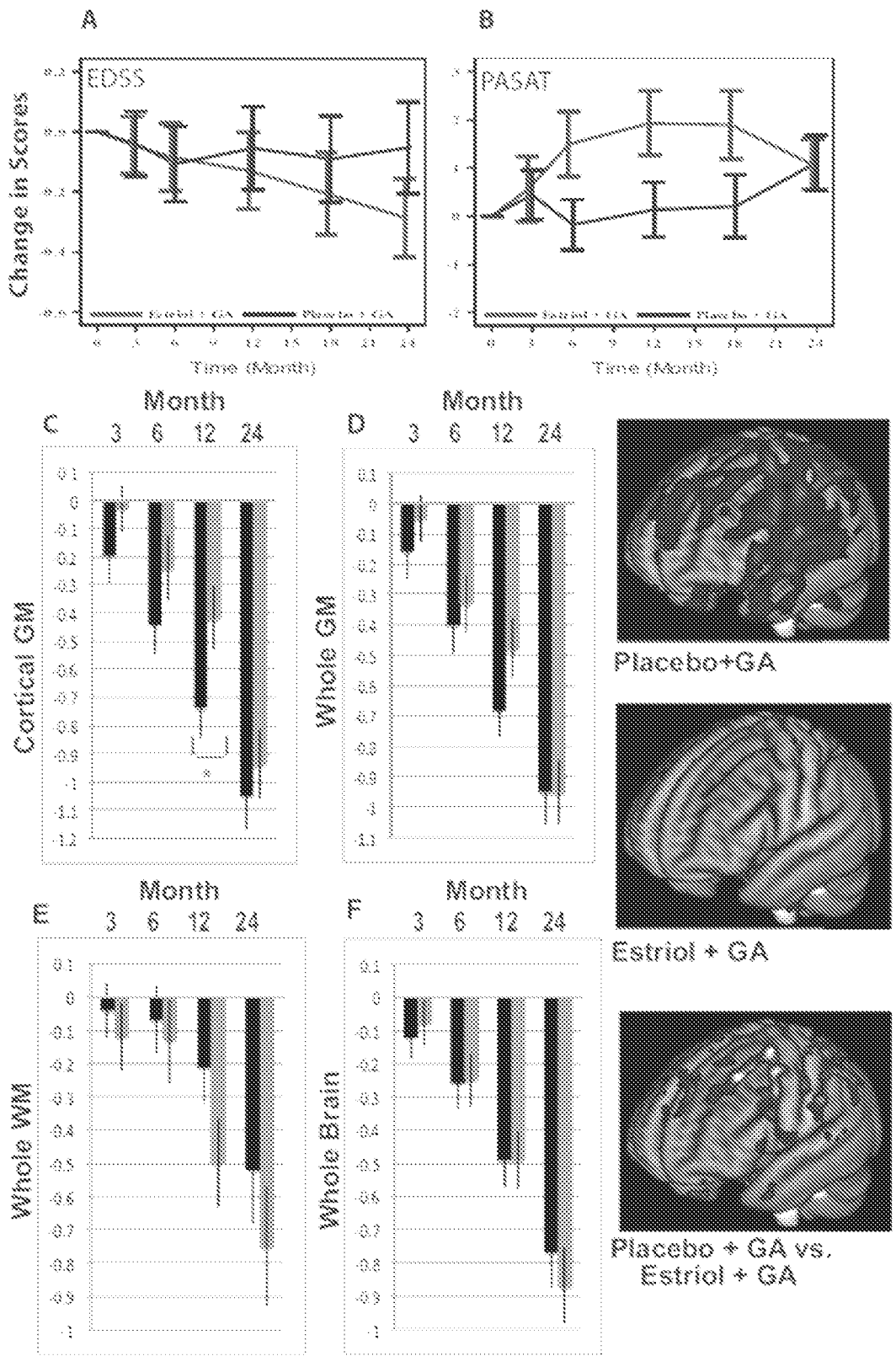
FIG. 7 includes nine panels, identified as panels (A), (B), (C), (D), (E), and (F). Panel (A) shows that EDSS improvement was observed at 24 months in the Estriol+GA within group comparison (median=−0.5, P=0.03), with no change in the Placebo+GA group (median=0, P=NS), and between groups comparison not reaching significance. (B) PASAT score improvement was observed at 12 months in the Estriol+GA within group comparison (P=0.005), with no change in the Placebo+GA group, and between group comparison significant (P=0.04), however scores assessed at the 24 month time point were no different between groups. All data are expressed as change in mean absolute scores over time as compared to baseline. (C-F) Change in volume from baseline for cortical gray matter in C; for whole gray matter in D; for whole white matter in E; and for whole brain in F. Right: Significant voxel-wise gray matter loss from baseline to month 12 was more in Placebo+GA (top left subpanel) than in Estriol+GA (top right panel), with regions showing significant between group differences demonstrated by intensity heat map (bottom panel). Disabilities are expressed as means+/−SE. Negative values indicate improvement for EDSS scores. Positive values indicate improvement for PASAT scores. EDSS=Expanded Disability Status Scale; PASAT=Paced Auditory Serial Addition Test (at 3 seconds). Volumes are expressed as mean percent change+/−SE from baseline. *=P<0.10, **=P<0.05. VBM results are visualized on the mean template and thresholded at P≤0.05, FDR corrected. Black indicates Placebo+GA, while Gray indicates Estriol+GA.
Figure 8:
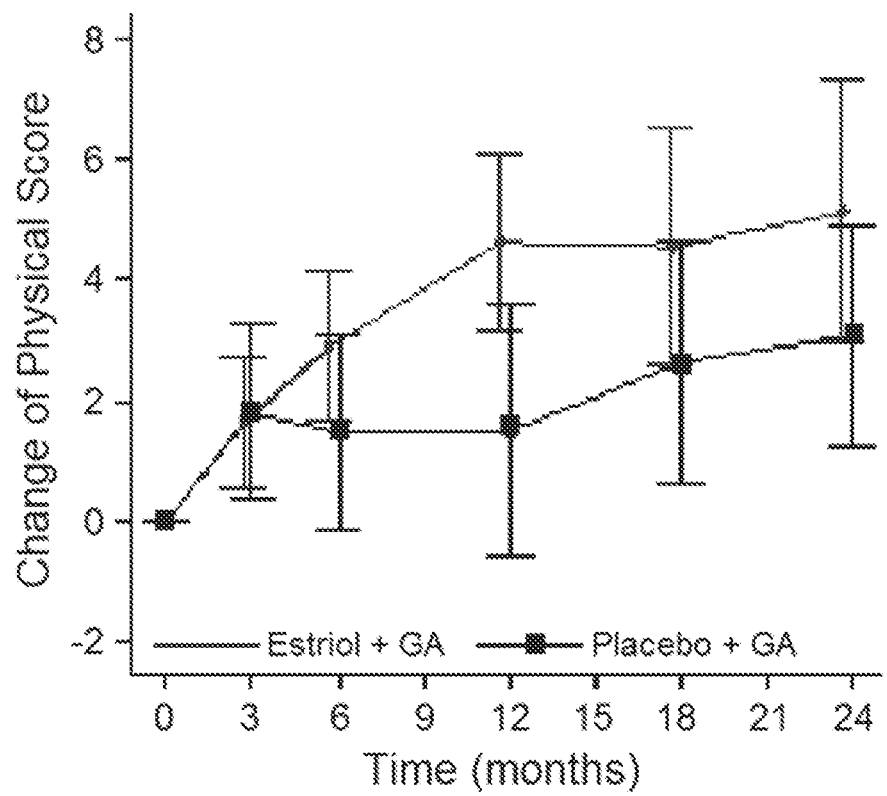
FIG. 8 shows MSQOL composite scores for Physical outcomes were improved in the Estriol+GA group (p=0.02), with no change in the Placebo+GA group, between group comparisons not reaching significance. All data are expressed as change in mean absolute scores over time as compared to baseline. Positive values indicate improvement for MSQOL Physical scores.
Figure 9:
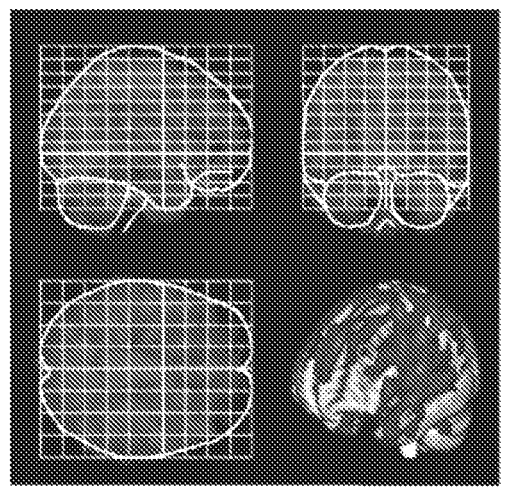
FIG. 9 shows maximum intensity projections of voxel-wise gray matter atrophy superimposed onto 3 orthogonal planes through the brain. At 12 months, significant localized gray matter loss was observed in the Placebo+GA group as compared to baseline (top) and in the Estriol+GA group as compared to baseline (middle), each shown in red in the 3 planes. Regions of significantly more gray matter loss in the Placebo+GA group as compared to the Estriol+GA group on between group comparisons are shown in yellow in the 3 planes (bottom). Gray matter loss is also visualized as projected onto a surface rendering of the mean template (lower right corner of each panel). All results are corrected for multiple comparisons by controlling the FDR at P≤0.05.
Figure 9:
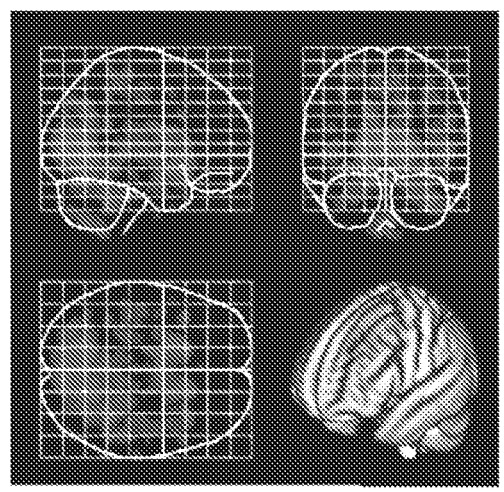
Figure 9:
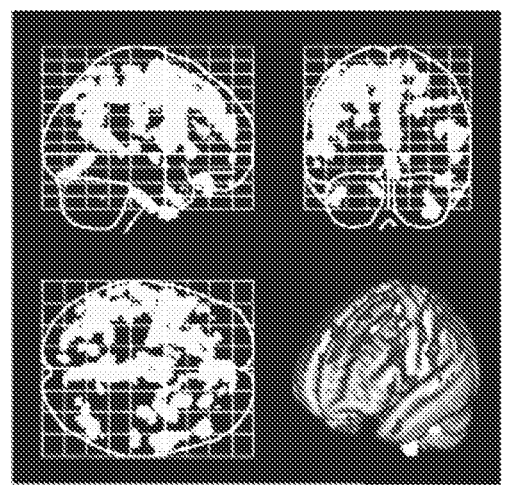

Gray matter volumes, specifically cortical gray matter volumes, have previously been associated with cognitive test scores. There was less cortical gray matter atrophy (45%) and whole gray matter atrophy (30%) at month 12 in the Estriol plus GA group compared to the Placebo plus GA group (cortical gray matter: Estriol+GA=−0.41, Placebo+GA=−0.74, p=0.079; whole gray matter: Estriol+GA=−0.47, Placebo+GA=−0.68, p=0.139) (FIGS. 7C & 7D). This gray matter sparing was independently confirmed using voxel-based morphometry (VBM), the latter revealing which gray matter regions were preserved with Estriol+GA compared to Placebo+GA (FIGS. 7 and 9). Similar to effects on PASAT scores, beneficial effects on gray matter sparing in the Estriol+GA group were no longer present at month 24. Indeed, correlations between PASAT improvement and gray matter sparing were found (cortical gray matter, p=0.0327; whole gray matter, p=0.0359), which was present in the Estriol+GA group (cortical gray matter, p=0.0159; whole gray matter, p=0.0093) and absent in the control Placebo+GA group. In contrast, the Estriol+GA group compared to the Placebo+GA group had more white matter atrophy.

TABLE 5

MRI Volumes

| | Estriol + GA (N = 82) | Placebo + GA (N = 76) | Comparing the two study groups§ |
|---|---|---|---|
| Enhancing Lesion Volume[a] | | | |
| Baseline (Mean ± SD, Median) | 79.7 ± 220, 0 | 54.2 ± 126, 0 | |
| Change from baseline at Mon 12 | N = 69 | N = 62 | |
| Mean ± SD, Median | −51.2 ± 202, 0 | −18.7 ± 184, 0 | −12.5 (−69.0-44.1) p = 0.665 |
| Change from baseline at Mon 24 | N = 55 | N = 55 | |
| Mean ± SD, Median | −39.3 ± 196, 0 | −34.0 ± 120, 0 | −1.6 (−62.6-59.5) p = 0.960 |
| Number of Enhancing Lesions[a] | | | |
| Baseline (Mean ± SD, Median) | 1.0 ± 2.3, 0 | 0.9 ± 2.1, 0 | |
| Change from baseline to Mon 12 | N = 68 | N = 62 | |
| Mean ± SD, Median | −0.9 ± 2.2, 0 | −0.5 ± 1.8, 0 | 0.89, (0.54-1.45) p = 0.631 |
| Change from baseline to Mon 24 | N = 55 | N = 55 | |
| Mean ± SD, Median | −0.9 ± 2.5, 0 | −0.5 ± 2.4, 0 | 0.89, (0.54-1.48) |

TABLE 5-continued

| | MRI Volumes | | |
|---|---|---|---|
| | Estriol + GA (N = 82) | Placebo + GA (N = 76) | Comparing the two study groups§ |
| Lesion activity on Brain MRI - proportion of patients with enhancing lesion | | | p = 0.655 |
| Baseline % (95% CI) | 32.1 (21.9-42.3) | 29.3 (19.0-39.6) | |
| Month 12 % (95% CI) | 14.5 (6.2-22.8) | 21.0 (10.8-31.1) | 0.30 (0.07-1.31) p = 0.110 |
| Month 24 % (95% CI) | 14.6 (5.2-23.9) | 14.6 (5.2-23.9) | 0.66 (0.13-3.40) p = 0.616 |
| Brain Volume - All Patients Baseline (Mean ± SD, Median) | | | |
| Whole brain | 1604 ± 62, 1607 | 1602 ± 51, 1602 | |
| Whole gray matter | 954 ± 51, 957 | 926 ± 52, 967 | |
| Cortical gray matter | 754 ± 46, 755 | 761 ± 42, 762 | |
| White matter | 650 ± 35, 650 | 640 ± 37, 635 | |
| % change from baseline (Mean ± SD, Median)[b] | | | |
| Whole Brain at Month 12 | −0.50 ± 0.70, −0.49 | −0.50 ± 0.64, −0.43 | −0.00 (−0.23-0.23) p = 0.988 |
| Month 24 | −0.89 ± 0.82, −1.0 | −0.78 ± 0.73, −0.91 | −0.02 (−0.26-0.22) p = 0.877 |
| Whole gray matter at Month 12 | −0.48 ± 0.82, −0.50 | −0.69 ± 0.71, −0.68 | 0.21 (−0.05-0.47) p = 0.108 |
| Month 24 | −0.96 ± 0.75 −0.94, | −0.95 ± 0.76, −0.93 | 0.12 (−0.16-0.39) p = 0.411 |
| Cortical gray matter at Month 12 | −0.44 ± 0.92, −0.51 | −0.72 ± 0.80, −0.67 | 0.29 (−0.01-0.58) p = 0.056 |
| Month 24 | −0.96 ± 0.86, −0.97 | −1.04 ± 0.87, −0.93 | 0.23 (−0.09-0.54) p = 0.156 |
| White matter at Month 12 | −0.51 ± 1.06, −0.16 | −0.20 ± 0.83, −0.11 | −0.29 (−0.63-0.04) p = 0.090 |
| Month 24 | −0.77 ± 1.28, −0.66 | −0.54 ± 1.12, −0.56 | −0.20 (−0.56-0.15) p = 0.261 |

Plus-minus values are means ± SD.
CI denotes confidence interval,
E + GA indicates Estriol + GA, and
P + GA indicates Placebo + GA.
[a]Change from baseline negative value indicates improvement.
[b]Change from baseline negative value indicates worsening.
§For Volume of Enhancing Lesions and Brain Volume (whole brain, gray matter, cortical gray matter and white matter, respectively), linear mixed effect model was developed using all follow-up data to estimate the difference of the value change from baseline between the two study groups at Months 24 and 12 while baseline value was adjusted.

For Number of Enhancing Lesions, the data in this column are E+GA vs. P+GA mean of lesions number ratio (95% CI) and p-value based on mixed effect negative binomial regression model.

For Lesion Activity on Brain MRI, the data in this column are E+GA vs. P+GA odds ratio (95% CI) and p-value based on mixed effect logistic regression model.

MRI Methodologies

MRI scans were performed at 0, 3, 6, 12 and 24 months using a standardized protocol implemented at each site that consisted of the following: T1-weighted 3D volume, pre and post contrast: TR2200, TE3.4, TI 900, 176 slices, 1 mm$^3$. Dual-echo fast spin echo: TR10000, TE12/95, 50 slices, 1×1×3 mm. Fluid attenuated inversion recovery (FLAIR): TR10380, TE88, TI88, TI2500, 50 slices, 1×1×3 mm. Minor changes were allowed to accommodate different platforms and field strengths at each site. MRI data in Dicom format were fully anonymized prior to transfer and then uploaded to the central MRI reading center database. Prior to study onset, each site provided a dummy scan utilizing the standardized sequences for review by the central MRI reading center to verify scan quality and fidelity. Quality control was maintained at each site using standard procedures for clinical scanners (daily phantoms, stability testing). Quarterly phantoms were collected from 12 of the 15 sites, most using the standard American College of Radiology (ACR) phatom. One site upgraded from a Siemens 1.5T to a 3.0T in November 2013, resulting in the acquisition of one month 24 scan on the new scanner. One site upgraded from a Phillips Achieva 3.0T to a Pillips Intera 3.0T after the first subject completed month 24. All subsequent studies were performed on the Intera.

Scans underwent a standard review locally by a radiologist blind to study details to assess for any new or unusual findings as a safety measure. Incoming imaging data was reviewed for completeness and fidelity to study pulse sequences by the imaging core investigators. Local radiologists and imaging core investigators were all blind to randomization assignment. All MRI investigators remained blinded to treatment assignment until the end of the study.

MRI brain, whole gray matter, whole white matter and cortical gray matter volumes were determined using a pairwise Jacobian integration (PJI) method. Pre-processing for structural T1-weighted images included 1) N3 non-uniformity correction, 2) histogram-based intensity normalization, 3) linear standard space registration using ICBM 2009c nonlinear symmetric template, 4) patch-based brain extraction, and 5) lesion-inpainting. Inputs to PJI were a pair of baseline and follow-up pre-processed structural T1-weighed images. The PJI consisted of 1) linear skull-constrained symmetric registration, 2) halfway transformation and resampling, 3) nonlinear symmetric registration using ANTS, and 4) voxelwise Jacobian determinant calculation on the warp field. Whole gray matter and whole white matter tissue masks were generated by SPM8 Segment function. Additional nonlocal means denoising was applied. For whole brain tissue masks, the whole gray matter and whole white matter masks were combined. For cortical gray matter mask, a standard cortical mask was nonlinearly transformed and merged with gray matter mask. The standard template was the ICBM (ICBM 2009c nonlinear symmetric version), and the nonlinear registration was performed by ANTS. Finally, the Jacobian determinants were averaged within the masks for percent volume change in cortical gray matter, whole gray matter, whole white matter, and whole brain.

Voxel-based morphometry (VBM) analyses were performed as described by Kurth et al. (Neuroimage Clin. 4:454 (2014)). All subjects included in the VBM cohort were required to have at least reached month 12 of the study, and all images had to pass quality control before and after image preprocessing to be included in the VBM cohort. Using this criteria, the VBM cohort consisted of Ill subjects (62 in the estriol+GA, and 49 in the placebo+GA group) from 13 sites for month 12 analyses, and 86 of these subjects (45 in the estriol+GA, and 41 in the placebo+GA group) for 24 month analyses.

Brain images were preprocessed utilizing SPM8 and the VBM8 toolbox. White matter lesions were in-painted to minimize their impact based on manual delineations that were used for the analysis of new T2 lesions. For this purpose, these manually delineated lesion masks were coregistered to the T1-weighted images, corrected if necessary, and used for lesion in-painting as described by Chard et al. (J. Magn. Reson. Imaging 34:223 (2010)). The lesion in-painted images were subsequently realigned for each subject using halfway-registrations and corrected for bias-field inhomogeneities. The realigned, bias corrected images were then tissue-classified into gray matter, white matter, and cerebrospinal fluid and registered to MNI space through linear and non-linearly transformations (see http://dbm.neuro.uni-jena.de/vbm8/VBM8-Manual.pdf). More specifically, the tissue classification was based on maximum a posteriori segmentations, accounted for partial volume effects, and was refined by applying a spatially adaptive non-local means denoising filter as well as a hidden Markov random field model. These methods made the tissue-classification independent of tissue probability maps and thus additionally minimized the influence of misclassifications, lesions, and altered geometry. Using DARTEL, the gray matter segments were then spatially normalized to the DARTEL Template supplied with the VBM8 Toolbox (see http://dbm.neuro.uni-jena.de/vbm), resulting in a voxel-wise comparability between subjects and time-points. Finally, the gray matter segments were smoothed with a Gaussian kernel (8 mm full width at half maximum). These smoothed gray matter segments constituted the input for the statistical analysis. For visualization, a mean template was created from the normalized brain images of all subjects, allowing the results from the statistical analysis to be related to the underlying mean anatomy of the subject sample.

VBM Statistical Analyses.

For the statistical analysis, a general linear model was applied that used the smoothed gray matter segments as the dependent and group x time as the independent variable. Subject and scan site were added as variables of no interest, thus effectively controlling for inter-individual differences (e.g. individual anatomy, age, disease duration, etc.) as well as the potentially confounding impact of different scanners. Non-sphericity was modeled and accounted for as described previously and implemented in SPM8. Applying this model, the interaction between group and time was calculated using T-tests to investigate group differences in local gray matter changes between month 0 and month 12 (month 0 and month 24, respectively). In addition, the gray matter loss within each group was investigated by calculating T-tests for month 0>month 12 (month 0>month 24, respectively) for each group separately. All results were corrected for multiple comparisons by controlling the false discovery rate (FDR) using a threshold of P≤0.05. Corrected results were rendered on the mean template of all subjects in FIG. 7. In addition, significant findings were visualized using maximum intensity projections as shown in FIG. 9.

Cognitive Testing

The estriol and placebo subjects were administered the 7/24 Spatial Recall Test periodically throughout the study. A perfect score on the test is 7, and for both treatment groups, the median score was also 7. Therefore, performance was assessed by the proportion of subjects in each group who achieved a perfect score on the test. The estriol group performed statistically better than the placebo group (Table 6). Logistic regression for repeated measurement was used to compare the probability having a perfect score between the two treatment groups, adjusting for age, education level, and baseline recall (Table 7).

TABLE 6

Percentage of subjects achieving a perfect score on the 7/24 Spatial Recall Test

| Month | Estriol + GA | Placebo + GA |
| --- | --- | --- |
| 0 | 65.8 (54/82) | 71.1 (54/76) |
| 3 | 72.5 (58/80) | 60.8 (45/74) |
| 6 | 70.5 (55/78) | 73.2 (52/71) |
| 12 | 74.3 (52/70) | 71.4 (45/63) |
| 18 | 88.9 (56/63) | 63.6 (35/55) |
| 24 | 76.3 (45/59) | 75.0 (42/56) |

TABLE 7

Odds ratio for achieving a perfect score on the 7/24 Spatial Recall Test

| Estimated perfect score rate (95% CI) | | Estriol vs. Placebo Odds ratio | |
| --- | --- | --- | --- |
| Estriol (%) | Placebo (%) | Odds ratio (95% CI) | P-value |
| 80.6 (74.9, 85.2) | 69.8 (63.4, 75.5) | 1.79 (1.18, 2.73) | P = 0.0067 |

The estriol and placebo subjects were administered the Delayed Recall Test periodically throughout the study. A perfect score on the test is 7, and for both treatment groups, the median score was also 7. Therefore, performance was assessed by the proportion of subjects in each group who achieved a perfect score on the test. The estriol group performed statistically better than the placebo group (Table 8). Logistic regression for repeated measurement was used to compare the probability having a perfect score between the two treatment groups, adjusting for age, education level, and baseline recall (Table 9).

TABLE 8

Percentage of subjects achieving a perfect score on the Delayed Recall Test

| Month | Estriol + GA | Placebo + GA |
|---|---|---|
| 0 | 67.1 (55/82) | 71.1 (54/76) |
| 3 | 75.0 (60/80) | 65.9 (48/74) |
| 6 | 73.1 (57/78) | 76.1 (54/71) |
| 12 | 68.6 (48/70) | 69.8 (44/63) |
| 18 | 85.7 (54/63) | 65.4 (36/55) |
| 24 | 79.7 (47/59) | 75.0 (42/56) |

TABLE 9

Odds ratio for achieving a perfect score on the Delayed Recall Test

| Estimated perfect score rate (95% CI) | | Estriol vs. Placebo Odds ratio | |
|---|---|---|---|
| Estriol (%) | Placebo (%) | Odds ratio (95% CI) | P-value |
| 81.8 (75.5, 86.8) | 73.2 (65.7, 79.5) | 1.65 (1.01, 2.70) | P = 0.0455 |

Example 3—Use of Copaxone® and Estriol for the Treatment of Multiple Sclerosis

Alternatively or in addition to all of the foregoing as it relates to gray matter, the invention further contemplates that white matter fA (fractional anisotropy) can be employed in a manner analogous to the gray matter atrophy as discussed herein in various embodiments.

Diffusion Tensor Imaging (DTI) assesses white matter, specifically white matter tract integrity. A decrease in fA can occur with either demyelination or with axonal damage or both. One can assess white matter substructures including optic nerve and cervical spinal cord.

MRIs of brain including high cervical spinal cord to be done at month 6, 1 year, and 2 years. If a decrease in fA of 10% is observed in fA of 2 tracts, treat with estriol to halt this decrease. Alternatively if fA is decreased by 10% in only one tract but that tract is associated with clinical deterioration of the disability served by that tract, treat with estriol. Poorer scores in low contrast visual acuity would correlate with decreased fA of optic nerve, while poorer motor function would correlate with decreased fA in motor tracts in cervical spinal cord.

INCORPORATION BY REFERENCE

All patents, published patent applications, and other publications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. As used herein, methods of treatment are equally applicable to uses of a composition described herein for treating the diseases or disorders described herein and/or compositions for use and/or uses of a composition described herein in the manufacture of a medicaments for treating the diseases or disorders described herein.

I claim:

1. A method of slowing or halting cortical gray matter atrophy in a human subject suffering from multiple sclerosis comprising
    administering orally to a subject in need thereof, on a continuous basis for a treatment period of 84 consecutive days (12 weeks), 8 mg of estriol daily;
    administering orally to the subject, for 14 consecutive days (2 weeks) of the treatment period, 0.7 mg of norethindrone daily; and
    wherein prior to administering the estriol the subject is receiving an immunotherapeutic agent or an anti-inflammatory agent.

2. The method of claim 1, further comprising administering to the patient an immunotherapeutic agent.

3. The method of claim 2, wherein the immunotherapeutic agent is selected from interferon-beta 1a, interferon-beta 1b, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

4. The method of claim 2, wherein the immunotherapeutic agent is glatiramer acetate.

5. The method of claim 4, wherein the is glatiramer acetate is administered subcutaneously to the subject on a continuous basis for the treatment period.

6. The method of claim 5, wherein the glatiramer acetate is subcutaneously administered to the subject in an amount of 20 mg daily.

7. The method of claim 1, wherein prior to administering the estriol the subject is receiving an immunotherapeutic agent.

8. The method of claim 1, wherein the method further comprises the steps of:
    assessing the change in the subjects cortical gray matter volume over a period of time; and
    administering the estriol to the subject in addition to the immunotherapeutic agent or an anti-inflammatory agent if the cortical gray matter volume decreases by at least 0.3 percent between a first assessment and a second assessment about 6 months after the first assessment, by at least 0.6 percent between a first assessment and a second assessment about one year after the first assessment, or by at least 1.0 percent between a first assessment and a second assessment about two years after the first assessment.

9. The method of claim 8, wherein the first assessment is performed before, at the same time as, or at about the same time as the subject receives the immunotherapeutic agent or anti-inflammatory agent.

10. The method of claim 8, wherein the second assessment is performed at least about six months, at least about one year, at least about 18 months, or at least about two years after said first assessment.

11. The method of claim 1, wherein the method comprises four consecutive treatment periods, five consecutive treatment periods, six consecutive treatment periods, seven consecutive treatment periods, or eight consecutive treatment periods.

12. The method of claim 11, wherein after four treatment periods the subject's gray matter atrophy is less than 1.5%, less than 1.4%, less than 1.3%, less than 1.2%, less than 1.1%, less than 1.0%, less than 0.9%, less than 0.8%, less than 0.7%, less than 0.6%, or less than 0.5% as compared to the start of administration.

13. The method of claim 11, wherein after four treatment periods the subject's gray matter atrophy is reduced by 3.5% as compared to a subject who has not been administered the estriol and norethindrone.

14. The method of claim 1, wherein the multiple sclerosis is relapsing-remitting multiple sclerosis.

15. The method of claim 1, wherein the multiple sclerosis is secondary-progressive multiple sclerosis.

16. The method of claim 1, wherein the multiple sclerosis is primary-progressive multiple sclerosis.

17. The method of claim 1, wherein the multiple sclerosis is progressive-relapsing multiple sclerosis.

18. The method of claim 1, wherein the estriol and norethindrone are formulated together.

19. The method of claim 1, wherein the subject is experiencing progression of the multiple sclerosis.

20. The method of claim 1, wherein the subject has progressive walking disability.

* * * * *